US007012683B2

(12) United States Patent
Wolf et al.

(10) Patent No.: US 7,012,683 B2
(45) Date of Patent: *Mar. 14, 2006

(54) APPARATUS AND METHODS FOR OPTICALLY INSPECTING A SAMPLE FOR ANOMALIES

(75) Inventors: Ralph C. Wolf, Palo Alto, CA (US); Eva L. Benitez, Sunnyvale, CA (US); Dongsheng (Don) Chen, Union City, CA (US); John D. Greene, Santa Cruz, CA (US); Jamie M. Sullivan, Sunnyvale, CA (US); Eric N. Vella, Mountain View, CA (US); Khiem D. Vo, Milpitas, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/993,473

(22) Filed: Nov. 18, 2004

(65) Prior Publication Data

US 2005/0092899 A1    May 5, 2005

Related U.S. Application Data

(63) Continuation of application No. 10/180,807, filed on Jun. 24, 2002, now Pat. No. 6,833,913.

(60) Provisional application No. 60/359,805, filed on Feb. 26, 2002.

(51) Int. Cl.
*G01N 21/88* (2006.01)

(52) U.S. Cl. .................................. 356/237.2
(58) Field of Classification Search .. 356/237.2–237.5; 250/205
See application file for complete search history.

(56) References Cited

U.S. PATENT DOCUMENTS 4,776,693 A    10/1988  Imamura ................. 356/237.3

(Continued)

FOREIGN PATENT DOCUMENTS

WO    WO98/23348    6/1998

(Continued)

*Primary Examiner*—Richard A. Rosenberger
(74) *Attorney, Agent, or Firm*—Beyer Weaver & Thomas, LLP

(57) ABSTRACT

Disclosed are methods and apparatus for detecting a relatively wide dynamic range of intensity values from a beam (e.g., scattered light, reflected light, or secondary electrons) originating from a sample, such as a semiconductor wafer. In other words, the inspection system provides detected output signals having wide dynamic ranges. The detected output signals may then be analyzed to determine whether defects are present on the sample. For example, the intensity values from a target die are compared to the intensity values from a corresponding portion of a reference die, where a significant intensity difference may be defined as a defect. In a specific embodiment, an inspection system for detecting defects on a sample is disclosed. The system includes a beam generator for directing an incident beam towards a sample surface and a detector positioned to detect a detected beam originating from the sample surface in response to the incident beam. The detector has a sensor for detecting the detected beam and generating a detected signal based on the detected beam and a non-linear component coupled to the sensor. The non-linear component is arranged to generate a non-linear detected signal based on the detected signal. The detector further includes a first analog-to-digital converter (ADC) coupled to the non-linear component. The first ADC is arranged to digitize the non-linear detected signal into a digitized detected signal.

19 Claims, 16 Drawing Sheets

U.S. PATENT DOCUMENTS

| | | | |
|---|---|---|---|
| 4,820,914 A | 4/1989 | Allen | 250/207 |
| 4,843,395 A * | 6/1989 | Morse | 341/156 |
| 4,905,286 A | 2/1990 | Sedgwick et al. | 704/233 |
| 5,047,769 A | 9/1991 | Engeler et al. | 341/118 |
| 5,076,692 A | 12/1991 | Neukermans et al. | 356/538 |
| 5,355,212 A * | 10/1994 | Wells et al. | 356/237.4 |
| 5,883,710 A | 3/1999 | Nikoonahad et al. | 356/237.2 |
| 5,991,699 A | 11/1999 | Kulkarni et al. | 702/82 |
| 6,002,122 A | 12/1999 | Wolf | 250/207 |
| 6,066,849 A | 5/2000 | Masnaghetti et al. | 250/310 |
| 6,081,325 A | 6/2000 | Leslie et al. | 356/237.2 |
| 6,104,835 A | 8/2000 | Han | 382/225 |
| 6,122,046 A | 9/2000 | Almogy | 356/237.2 |
| 6,178,257 B1 | 1/2001 | Alumot | 382/145 |
| 6,208,750 B1 | 3/2001 | Tsadka | 382/145 |
| 6,288,780 B1 * | 9/2001 | Fairley et al. | 356/237.1 |
| 6,437,862 B1 * | 8/2002 | Miyazaki et al. | 356/237.2 |
| 6,833,913 B1 * | 12/2004 | Wolf et al. | 356/237.2 |

FOREIGN PATENT DOCUMENTS

| | | |
|---|---|---|
| WO | WO99/13082 | 3/1999 |
| WO | WO99/14056 | 3/1999 |
| WO | WO99/25549 | 5/1999 |
| WO | WO00/13042 | 3/2000 |
| WO | WO00/16020 | 3/2000 |
| WO | WO00/22410 | 4/2000 |
| WO | WO00/27777 | 5/2000 |
| WO | WO01/140145 | 6/2001 |

* cited by examiner

APPARATUS AND METHODS FOR OPTICALLY INSPECTING A SAMPLE FOR ANOMALIES

CROSS REFERENCE TO RELATED APPLICATIONS

This application claims priority of U.S. patent application Ser. No. 10/180,807, filed 24 Jun. 2002 now U.S. Pat. No. 6,833,013 by Ralph C. Wolf et al, which claims priority of U.S. Provisional Patent Application No. 60/359,805, filed 26 Feb. 2002 by Ralph C. Wolf et al., which application is incorporated herein by reference in its entirety for all purposes.

BACKGROUND OF THE INVENTION

The present invention relates generally to inspection systems. More specifically, it relates to light collection mechanisms for inspecting semiconductor wafers and other types of patterned samples.

Conventional darkfield optical inspection tools locate defects on patterned wafers by scanning the surface of the wafer with a tightly focused laser spot and measuring the amount of light scattered by the illuminated spot on the wafer. Dissimilarities in the scattering intensity between similar locations in adjacent dies are recorded as potential defect sites.

The dynamic range of this optical scattering is typically substantial. Changes in scattering intensity of more than a million to one within a single die are not uncommon. This high dynamic range is intrinsic to the optical configuration of the instrument and the scattering properties of the wafers and defects of interest. Because this dynamic range is substantially greater than the reliable measurement range of existing instruments, inspection operators are forced to accept an unpleasant compromise between inspecting with too low a sensitivity in some portions of the die, and temporarily overloading the instrument's detection electronics in other regions.

In general, scanning the wafer with the smallest possible laser spot size maximizes sensitivity to defects by maximizing the spatial resolution of the scattering image. However, this increased resolution generally correlates with an increased pixel density within the light collectors or detectors to properly sample the image. The detectors typically include a sensor for detecting the scattered light and generating an analog signal based on such detected light and an analog-to-digital converter (ADC) for converting the analog detected signal into a digital detected signal. The digital detected signal may then be analyzed for defects. Since all the pixels are measured serially, and only a limited amount of time is available to scan each wafer, there is a fundamental relationship between the speed of the measurement electronics and the maximizing of the spatial resolution of the scattering image. To enable high spatial resolution, higher bandwidth analog electronics and faster ADC's are often utilized.

In addition to maximizing the speed of the measurement electronics to thereby maximize spatial resolution, it is desirable to maximize the dynamic range of the light that is discernable by the measurement electronics. However, there is a fundamental trade-off in ADC's between speed and dynamic range. That is, dynamic range is typically limited by noise and offset errors, both of which tend to increase with speed.

Accordingly, there is a need for improved inspection mechanisms that are capable of quickly detecting light having a relatively high dynamic range.

SUMMARY OF THE INVENTION

Accordingly, mechanisms are provided for detecting a relatively wide dynamic range of intensity values from a beam (e.g., scattered light, reflected light, or secondary electrons) originating from a sample, such as a semiconductor wafer. In other words, the inspection system provides detected output signals having wide dynamic ranges. The detected output signals may then be analyzed to determine whether defects are present on the sample. For example, the intensity values from a target die are compared to the intensity values from a corresponding portion of a reference die, where a significant intensity difference may be defined as a defect.

In a specific embodiment, an inspection system for detecting defects on a sample is disclosed. The system includes a beam generator for directing an incident beam towards a sample surface and a detector positioned to detect a detected beam originating from the sample surface in response to the incident beam. The detector has a sensor for detecting the detected beam and generating a detected signal based on the detected beam and a non-linear component coupled to the sensor. The non-linear component is arranged to generate a non-linear detected signal based on the detected signal. The detector further includes a first analog-to-digital converter (ADC) coupled to the non-linear component, and the first ADC is arranged to digitize the non-linear detected signal into a first digitized detected signal. The system further includes a data processor for determining whether there is a defect present on the sample surface based on the first digitized detected signal.

In a further aspect, the system also includes a transformation mechanism for transforming the first digitized detected signal into a second digitized detected signal that compensates for noise variation associated with different intensity levels of the first detected output signal. The data processor is farther arranged to receive the second digitized signal and the step of determining whether there is a defect is based indirectly on the first digitized detected signal by being based directly on the second digitized detected signal. In a further implementation, the transformation mechanism operates to cause a derivative of the second digitized detected signal to be equal to a normalization function, which is an estimate of the inverse of the noise level or uncertainty in the measurement. One such normalization function may be computed by dividing an average of an envelope function by the envelope function itself, the envelope function being calculated based on an observed repeatability of measurements of the first digitized detected signal.

In one aspect, the sensor is a photomultiplier tube (PMT). In other implementations, the sensor is an electron multiplier tube, a micro-channel plate PMT, an avalanche photodiode, a metal channel dynode PMT, a wire mesh dynode PMT, a PMT with explicit gate or grid electrodes, or an imaging array with programmable integration time.

In one aspect, the non-linear component is a logarithmic amplifier. In a further aspect, the detector further includes a first feed back circuit for automatically adjusting a sensor gain of the sensor based on the non-linear detected signal or the detected signal. In one embodiment, the first feed back circuit has a variable voltage supply component coupled to the non-linear component and arranged to adjust a voltage level of the sensor gain based on non-linear detected signal or the detected signal, a voltage reference signal, and one or more control signal(s). The first feed back circuit further includes an amplifier coupled to the variable voltage supply and arranged to amplify the sensor gain signal prior to it being input to the sensor.

In a further embodiment, the system further includes a second ADC for receiving the sensor gain, digitizing the sensor gain and outputting it as a digitized sensor gain signal. The system also has a first transformation mechanism for calibrating the digitized detected signal into a calibrated detected signal and a second transformation mechanisms for calibrating the digitized sensor gain signal into a calibrated gain signal. The system further includes an arithmetic logic unit (ALU) arranged to subtract the calibrated gain signal from the calibrated detected signal to form a first detected output signal. Preferably, the first and second transformation mechanisms take the form of a look-up table embodied within a memory device, but they may also be implemented as a mathematical equation which is evaluated by a digital computer, digital signal processor, or programmable logic device. The data processor is further arranged to receive the first detected output signal and the step of determining whether there is a defect is based indirectly on the first digitized detected signal by being based directly on the first detected output signal In yet a further aspect, the system includes an offset mechanism arranged to receive a user-selected sensor gain and offset the first detected output signal by a log of the user-selected gain to thereby emulate a programmable sensor gain, where the sensor gain is not altered. In a further aspect, the first and second transformation mechanisms and the ALU have a higher resolution than the first and second ADCs, in order to avoid rounding errors in the transformations.

In another aspect, the system includes a second linear or non-linear amplifier (e.g., a logarithmic amplifier) arranged to receive an illumination level of the incident beam, followed by a third ADC and third transformation mechanism which determines the logarithmic value of the illumination level to produce a log illumination level. The ALU is further arranged to subtract the log illumination level from the first detected signal. In a further embodiment, the system includes a second feed back circuit for automatically adjusting the illumination level based on the sensor gain, the non-linear detected signal or the detected signal.

In yet another aspect, the system includes a third transformation mechanism for transforming the first detected output signal into a second detected output signal. The second detected output signal is a relinearized first detected output signal when a mode signal input to the third transformation mechanism indicates a first mode and the second detected output signal equaling the first detected output signal when the mode signal indicates a second mode. In a further embodiment, the second detected output signal equals a noise compensating transformation of the first detected output signal when the mode signal indicates a third mode. The data processor is further arranged to receive the second detected output signal and the step of determining whether there is a defect is based indirectly on the first digitized detected signal by being based directly on the second detected output signal.

In an alternative embodiment, an inspection system for detecting defects on a sample is disclosed. The system has a beam generator for directing an incident beam towards a sample surface and a detector positioned to detect a detected beam originating from the sample surface in response to the incident beam. The detector includes a sensor for detecting the detected beam and generating a detected signal based on the detected beam, a logarithmic amplifier coupled to the sensor and arranged to generate a logarithmic detected signal based on the detected signal, and a first analog-to-digital converter (ADC) coupled to the logarithmic amplifier, the first ADC being arranged to digitize the logarithmic detected signal into a digitized detected signal. The detector also includes a first look-up table embodied in a first memory device and arranged to calibrate the digitized detected signal into a calibrated detected signal and a feed back circuit for automatically adjusting a sensor gain of the sensor based on the logarithmic detected signal or the detected signal, the sensor gain being input to the sensor. The detector also includes an amplifier arranged to amplify the sensor gain to an amplified sensor gain and a second ADC coupled to the amplifier and arranged to digitize the amplified sensor gain into a digitized sensor gain. The detector also has a second look-up table embodied in a second memory device and arranged to calibrate the digitized sensor gain signal into a calibrated sensor gain signal and an arithmetic logic unit (ALU) arranged to subtract the calibrated gain signal from the calibrated detected signal to form a first detected output signal.

In a further implementation, the system includes a third look-up table embodied in a third memory device and arranged to transform the first detected output signal into a second detected output signal to facilitate data processing and a data processor arranged to analyze the second detected output signal to determine whether there is a defect on the sample surface. In a further implementation, the second detected output signal is a relinearized first detected output signal when a mode signal input to the third look-up table indicates a first mode and the second detected output signal equaling the first detected output signal when the mode signal indicates a second mode. In a further embodiment, the second detected output signal equals a noise compensating transformation of the first detected output signal when the mode signal indicates a third mode. In a final aspect, the inspection system includes an offset mechanism arranged to receive a user-selected sensor gain and offset the first detected output signal by a log of the user-selected gain to thereby emulate a programmable sensor gain, where the sensor gain is not altered. The ALU is further arranged to add the log user-selected sensor gain to the first detected output signal.

In another embodiment, the invention pertains to a method for detecting defects on a sample. An incident beam is directed towards a first sample surface. A first detected beam is detected and a first detected signal is generated based on the first detected beam. The first detected beam originates from the first sample surface in response to the incident beam. A first non-linear detected signal is generated based on the first detected signal. The first non-linear detected signal is digitized into a first digitized detected signal, and the first digitized detected signal is analyzed to determine whether it corresponds to a defect on the first sample surface. A first sensor gain of the sensor is automatically adjusted based on the first non-linear detected signal or the first detected signal.

In a further aspect, an incident beam is directed towards a second sample surface. A second detected beam is detected and a second detected signal is generated based on the second detected beam. The second detected beam originates from the second sample surface in response to the incident beam. A second non-linear detected signal is generated based on the second detected signal, and the second non-linear detected signal is digitized into a second digitized detected signal. A second sensor gain of the sensor is automatically adjusted based on the second non-linear detected signal or the second detected signal.

The first and second digitized detected signals are logarithmic values. The first digitized detected signal is analyzed by subtracting the second digitized detected signal, the subtraction resulting in a difference of a log of intensity values from the first and second sample surfaces, which corresponds to the log of the ratio of the intensities. It is determined that the first digitized detected signal corresponds to a defect on the first sample surface when the difference is above a predetermined threshold.

In an alternative embodiment, the inspection system includes a beam generator for directing an incident beam towards a sample surface and a beam splitter for receiving a detected beam from the sample surface which is responsive to the incident beam and splitting the detected beam into a first fraction and a second fraction, wherein the first fraction is significantly larger than the second fraction. The system further includes a high gain sensor for receiving the first fraction of the detected beam and generating a first detected signal based on the first fraction and a low gain sensor for receiving the second fraction of the detected beam and generating a second detected signal based on the second fraction. The system further includes a control block coupled with the low gain sensor and operable to regulate a gain of the high gain sensor based on the second detected signal and to output an invalid signal indicative of a reliability factor of the first detected signal, a first ADC for receiving the first detected signal, digitizing it, and outputting a first digital detected signal, a second ADC for receiving the second detected signal, digitizing it, and outputting a second digital detected signal, and a data processor for receiving the first and second digital detected signals and the invalid signal and determining whether there is a defect present on the sample surface. The determination is based on the first digital detected signal when the Invalid signal indicates that the first digital detected signal is reliable and based on the second digital detected signal when the Invalid signal indicates that the first digital detected signal is unreliable In one aspect, the step of determining whether there is a defect present on the sample surface is accomplished by analyzing the first and second digital detected signals separately to determine whether there is a defect on the sample surface and reporting any defect found during the analysis of the first digital detected signal only when the Invalid signal indicates that the first digital detected signal is reliable. The determination is further accomplished by reporting any defect found during the analysis of the second digital detected signal only when the Invalid signal indicates that the first digital detected signal is unreliable.

In another aspect the step of determining whether there is a defect present on the sample surface is accomplished by selecting a first operating voltage for the high gain sensor and a second operating voltage for the low gain sensor so that a ratio of the effective gains of the high gain sensor and the low gain sensor is equal to the Mth power of two, where M is an integer. The determination is further accomplished by forming an output data word from the first digital detected signal by padding the first digital detected signal with M zeros on the most significant bit side when the Invalid signal indicates that the first digital detected signal is reliable. Otherwise, the output data word is formed from the second digital detected signal by shifting the second digital detected signal M bits towards the most significant bit side and padding the shifted signal with M zeros on the least significant bit side, when the Invalid signal indicates that the first digital detected signal is unreliable. In a specific implementation, the control block is operable to regulate the gain of the high gain sensor by automatically adjusting the gain of the sensor based on the second detected signal or the second fraction. In a further implementation the control block is operable to regulate the gain of the high gain sensor by turning off the high gain sensor or indicating to the high gain sensor that it should turn off when the second detected signal or the second fraction rises above a predetermined threshold and turning the high gain sensor back on or indicating to the high gain sensor that is should turn back on when the second detected signal or the second fraction falls back below the predetermined threshold.

These and other features and advantages of the present invention will be presented in more detail in the following specification of the invention and the accompanying figures which illustrate by way of example the principles of the invention.

DETAILED DESCRIPTION OF SPECIFIC EMBODIMENTS

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

In general terms, the inspection systems of the present invention is capable of detecting a relatively wide dynamic range of intensity values from a beam (e.g., scattered light, reflected light, or secondary electrons) originating from a sample, such as a semiconductor wafer. In other words, the inspection system provides detected output signals having wide dynamic ranges. The detected output signals may then be analyzed to determine whether defects are present on the sample. For example, the intensity values from a target die are compared to the intensity values from a corresponding portion of a reference die, where a significant intensity difference may be defined as a defect. These inspection systems may implement any suitable inspection technology, along with the novel illumination, defect detection, and defect analysis mechanisms described further below. By way of examples, brightfield and/or darkfield optical inspection mechanisms may be utilized. Suitable optical inspection systems in which the mechanisms of the present invention may be incorporated are described further in U.S. Pat. No. 6,081,325, U.S. Pat. No. 5,355,212, U.S. Pat. No. 5,883,710, U.S. Pat. No. 6,178,257, U.S. Pat. No. 6,122,046 and U.S. Pat. No. 6,208,750, PCT Application PCT/US00/22410, PCT Application PCT/US00/13042, PCT Application PCT/US99/14056, PCT Application PCT/US99/13082, PCT Application PCT/US98/23348, PCT Application PCT/US99/25549, PCT Application PCT/US00/16020, and European Patent Application 00112703.4, which patents and applications are incorporated herein by reference in their entirety. The mechanisms of the present invention may also be implemented within a scanning electron microscopy system as described further below with respect to FIG. 14.

Figure 1:
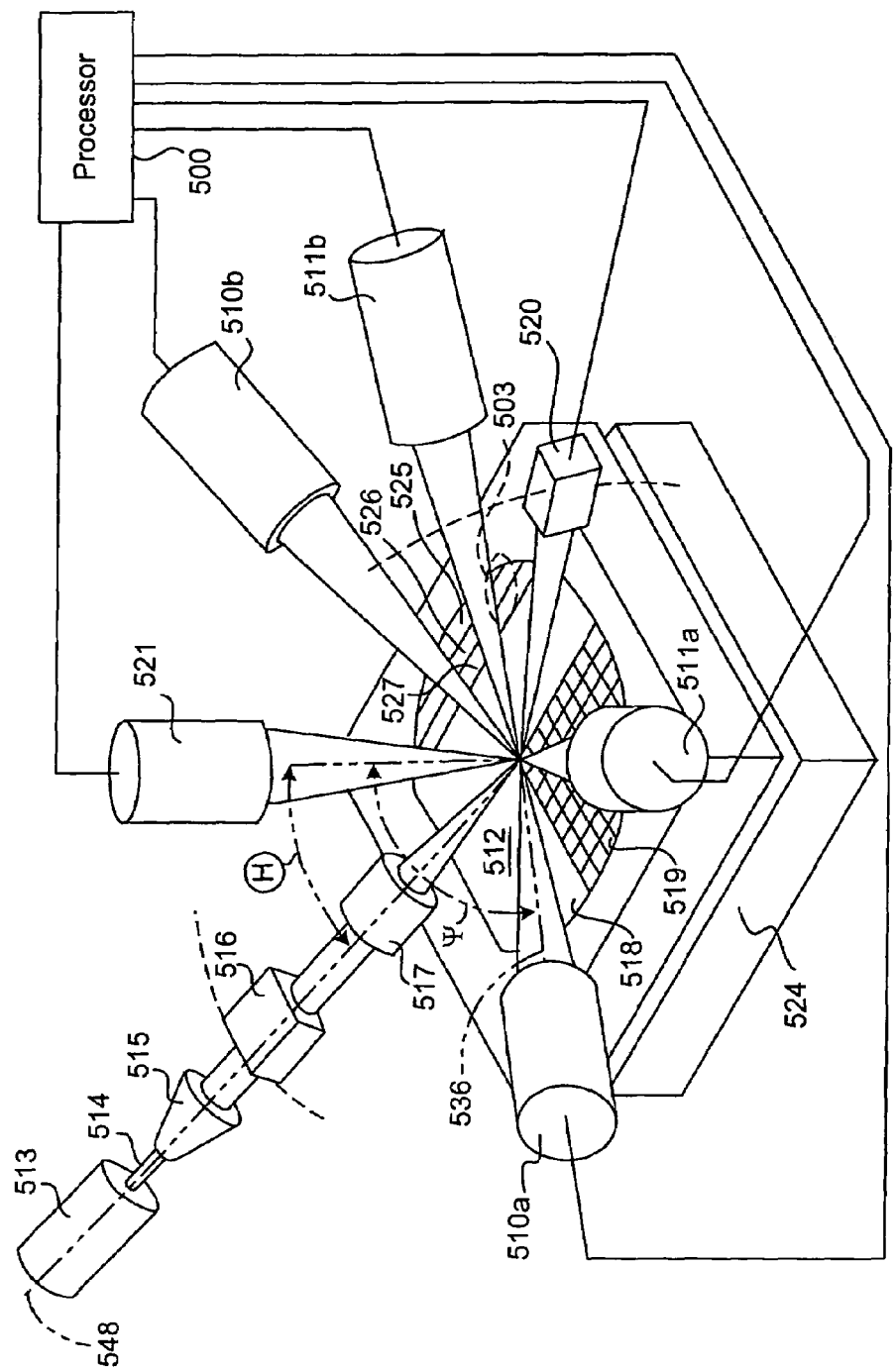
FIG. 1 is a diagrammatic representation of an optical inspection system in accordance with one embodiment of the present invention.

FIG. 1 is a diagrammatic representation of an optical system in accordance with one embodiment of the present invention. The optical system includes any suitable number of detectors or collection channels for detecting light emitted from a sample, such as a semiconductor surface. The detectors or collection channels may be arranged in any suitable position and depend on the particular requirements of the inspection application. The illustrated embodiment uses two groups of two collector channels, 510a–b and 511a–b, disposed symmetrically about the wafer surface 512 so that each collector channel within a pair is located at the same azimuthal angle on opposite sides of the scan line, indicated by the line B. These azimuthal collector channels detect scattered light.

The output from the collector channels may then be sent to processor 500 for data analysis and/or image generation. The data from the channels is compared by performing various algorithms and logical operations, e.g., OR, AND and XOR.

The optical system also includes a beam generator (e.g., components 513, 515, 516, and 517) for generating an incident beam and directing it towards a sample. As shown in FIG. 1, a light source 513, typically a laser, emits a beam 514. Beam 514 is directed towards a pre-deflector optics 515, which consists of a half wave-plate, a spatial filter and several cylindrical lenses, in order to produce an elliptical beam with a desired polarization that is compatible with the scanner 516. The pre-deflector optics 515 expands the beam 514 to obtain the appropriate numerical aperture. The post-deflector optics 517 includes several cylindrical lenses and an air slit. Finally, the beam 514 is brought into focus on the a wafer surface 512 and scanned along the direction, in the plane of the wafer surface 512, indicated by B, perpendicular to the optical axis of the beam 514. The type of deflector employed in the apparatus is application dependent and may include a polygonal mirror or galvonmeter. In one embodiment, deflector 516 is an Acousto-optic Deflector. The wafer surface 512 may be smooth 518 or patterned 519. In addition to the collector channels 510a–b and 511a–b, described above, detector channels may be provided which include a reflectivity/autoposition channel 520, and a normal collector channel 521 each of which are discussed more fully below.

The wavelength of the beam 514 depends on the particular requirements of the application. In the illustrated embodiment, the beam 514 has a wavelength of about 488 nm and is produced by any suitable light source, such as an Argon ion laser. The optical axis 548 of the beam 514 is directed onto the wafer surface 512 at an angle θ. This angle θ is preferably in the range of 55–85 degrees with respect to the normal to the wafer surface 512, depending on the application. The scanning mechanism includes the deflector 516 and the translation stage 524 upon which the wafer rests. The position of the wafer on the stage 524 is maintained in any convenient manner, e.g., via vacuum suction. The stage 524 moves to partition the surface 512 into striped regions, shown as 525, 526 and 527 with the deflector 516 moving the beam across the width of the striped regions.

Figure 3:
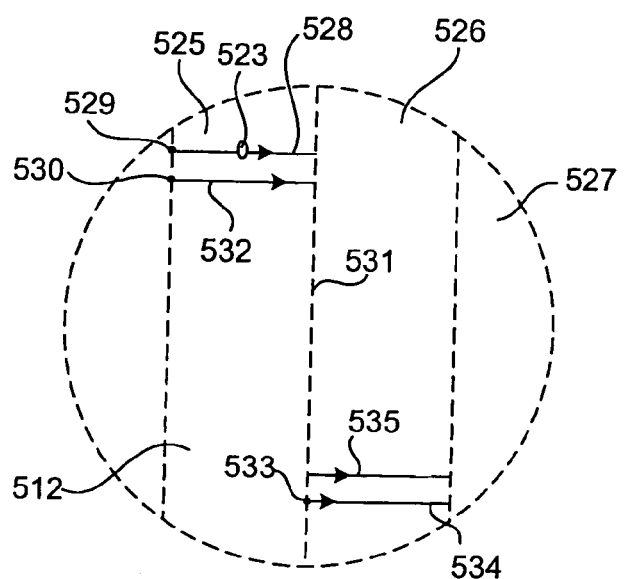
FIG. 3 is a detailed view showing the scan path of a spot on a wafer surface in accordance with one embodiment of the present invention.

Referring to FIG. 3, the grazing angle of the beam 514 produces an elliptical spot 523 on the wafer surface 512, having a major axis perpendicular to the scan line. The deflector 516 scans the spot 523 across a short scan line equal in length to the width of striped region 525 to produce specularly reflected and scattered light. The spot 523 is scanned in the direction indicated, as the stage 524 moves the wafer perpendicular to the scan line. This results in the spot 523 moving within the striped region 525, as shown in FIG. 3. In the illustrated embodiment, the spot 523 scans in the direction as indicated by scan path 528. Scan path 528 has an effective start location at 529 and the spot 523 moves to the right therefrom until is reaches the border 531 of striped region 525. Upon reaching border 531, the spot 523 moves relative to the stage 524 perpendicular to the scan direction and the spot assumes a new start position 530 and moves parallel to scan line 528, along scan line 532. The deflector 516 continues to scan the spot 523 in this fashion along the entire length of striped region 525. Upon completion of the scan of striped region 525, the stage 524 moves relative to the wafer to permit the scanning of the adjacent striped region 526. The effective start location 533 is positioned so that the stage 524 shall move perpendicular to each scan line in a direction opposite to that when scanning striped region 524, thereby forming a serpentine scan. This is demonstrated by scan paths 534 and 535. Moving the stage 524 to scan adjacent striped regions in opposite directions substantially reduces the amount of mechanical movement of the stage while increasing the number of wafers scanned per hour.

Figure 2:
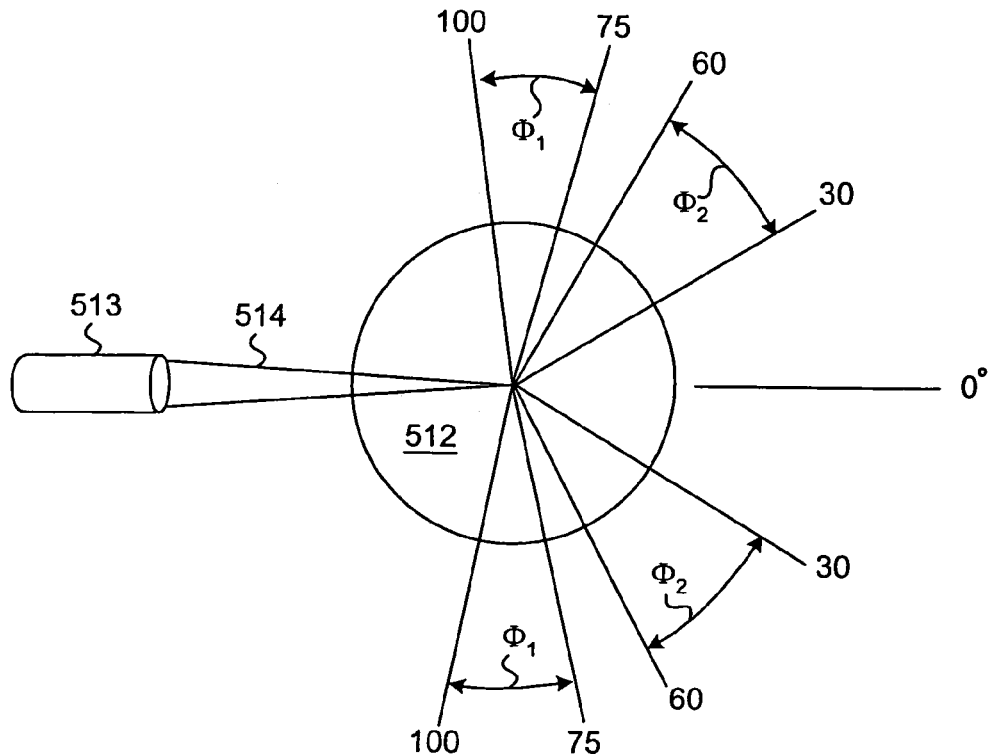
FIG. 2 is a top view of the illumination and collection channels of FIG. 1 in accordance with one embodiment of the present invention.

Referring to FIGS. 1 and 2, light scattered from the wafer surface 512 is detected by a plurality of detectors, including collector channels 510a–b and 511a–b. The collector channels collect light over a fixed solid angle, dependent upon, inter alia, the elevational and azimuthal angle of the channel. The optical axis of each collection channel is positioned at an angle of elevation $\psi$ in the range of 0 to 90 degrees with respect to the normal to the surface 512. As discussed above collector channels 510a and 510b are symmetrically positioned at the same azimuthal angle with respect to beam 514, on opposite sides of the scan line. Collector channels 510a and 510b are positioned, with respect to the beam 514, at an azimuthal angle $\psi_1$ in the range of about 75 to about 105 degrees to collect laterally scattered light. Laterally scattered light is defined as light scattered at azimuthal angles in the range of about 75 to about 105 degrees, with respect to beam 514. Similar to collector channels 510a and 510b, channels 511a and 511b are positioned on opposite sides of the scan line at the same azimuthal angle; however, the azimuthal angles $\psi_2$ of channels 511a and 511b are in the range of 30 to 60 degrees, to collect forwardly scattered light. Forwardly scattered light is defined as light scattered at azimuthal angles in the range of 30 to 60 degrees. Those of ordinary skill in the art will readily recognize that the number and location of the collector channels and/or their collection solid angle may be changed in various alternative embodiments without departing from the scope of the invention.

The bright field reflectivity/autoposition channel 520, is positioned in front of the beam 514 to collect specularly reflected light. The bright field signal derived from this channel carries information concerning the pattern, local variations in reflectivity and height. This channel is sensitive to detecting various defects on a surface. For example, the bright field signal is sensitive to representing film thickness variations, discoloration, stains and local changes in dielectric constant. The bright field signal is also used to produce an error height signal, corresponding to a variation in wafer height, which is fed to a z-stage to adjust the height accordingly. Finally, the bright field signal can be used to construct a reflectivity map of the surface. This channel is basically an unfolded Type I confocal microscope operating in reflection mode. It is considered unfolded because the illuminating beam and reflected beams, here, are not collinear, where as, in a typical reflection confocal microscope the illuminating and reflected beams are collinear.

The normal collector channel collects light over a fixed solid angle over a region which is approximately perpendicular to the plane of the wafer. Other than the collection solid angle, the normal collector implementation is similar to the other collector channels 510ab and 511ab. The normal collector is used to collect scattered light from the intentional patterns on the wafer, as well as to detect defects which scatter light in an upwards direction. Signals collected from the intentional patterns are used to facilitate the alignment and registration of the wafer pattern to the coordinate system of the mechanical stage in the instrument.

One or more of the collector channels include mechanism for increasing the dynamic range of detected output signals. Preferably, these mechanisms for increasing dynamic range are provided within collector channels 510ab, 511ab and 521. In general terms, a high dynamic range collector includes a light sensor, such as a photomultiplier tube (PMT) for generating a signal from detected photons and an analog to digital converter (ADC) for converting the light signal to a digital light signal. Of course, other suitable mechanism may be used for sensing light and converting an analog signal into a digital signal.

The high dynamic range collector also includes mechanisms for increasing the dynamic range. In one embodiment, the collector includes a high-speed feedback mechanism to continuously modulate the gain of the PMT in response to the detected signal level. The PMT gain and PMT detected output signal are then independently passed through non-linear mechanisms. For example, the PMT detected output is passed through a logarithmic amplifier, and the PMT gain and the PMT detected output signal are then independently transformed into ideal logarithmic output signals. The resulting non-linear signals are then subtracted from one another (e.g., the log-space equivalent of division) to reconstruct a non-linear (e.g., logarithmic) representation of the detected optical signal. By this method, the dynamic range of the detected signal can be extended to at least 6 orders of magnitude, for continuously varying signals with bandwidth of up to 25 MHz, and possible more. The logarithmic output data is more easily manipulated than linear data. For example, division and multiplication operations may be performed with the detected data. This logarithmic transformation also increases the dynamic range of the detected signal.

In an alternative embodiment, simply placing non-linear components between the sensor output and the corresponding ADC gives an overall increased dynamic range for the sensor output. The non-linear components match the dynamic range of the sensor output more closely to the ADC's dynamic range. For example, a logarithmic amplifier may be placed between the PMT output and corresponding ADC.

In particular applications, the inspection system may also include mechanisms for transforming the non-linear (e.g., logarithmic) output signals so as to emulate signals from a conventional linear detection system. For example, logarithmic output data may be relinearized. The output from a conventional "fixed" mode detector system, where the PMT gain is not continuously adjusted but set by a user to a "fixed" value, may also be emulated. This capability may be selectable. In other words, one may select between a "fixed" mode and an "adaptive" mode, where the output corresponds to output from a non-linear detection system where the PMT gain is continuously adjusted. The output data may also be transformed to compensate for noise variations.

The inspection system of the present invention may include any combination of these capabilities. For example, a system may include a detector utilizing any combination of continuous PMT gain adjustment mechanisms, mixed mode mechanisms for switching between fixed and adaptive modes, logarithmic data transformations, noise compensation mechanisms, and/or non-linear components placed between the sensor output and its corresponding ADC. Several inspection embodiments which implement one or more of these mechanisms are further described below with reference to FIGS. 4 through 14.

Figure 4:
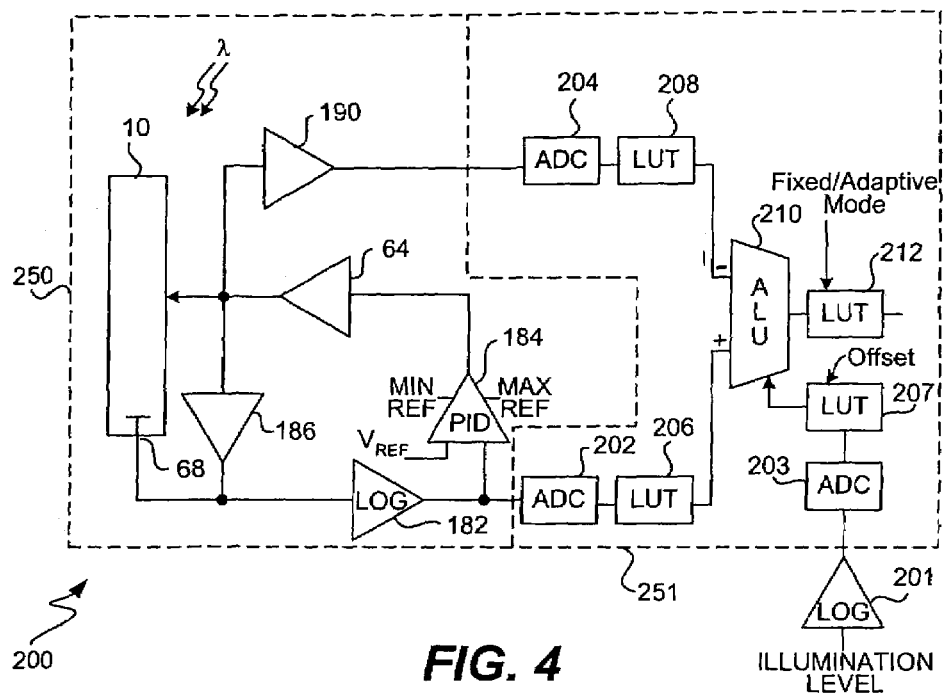
FIG. 4 is a schematic diagram illustrating a mixed mode detector (MMD) having continuous gain adjustment and logarithmic transformation, as well as mixed mode, capabilities according to one embodiment of the present invention

FIG. 4 is a schematic diagram illustrating a mixed mode detector (MMD) 200 having continuous gain adjustment and logarithmic transformation, as well as mixed mode, capabilities according to one embodiment of the present invention. As shown, the MDD 200 includes a sensor or measurement block 250 and an output processor 251. The measurement block 250 generally senses a beam emitted from the sample and generates a detected signal based on the sensed beam. The measurement block 250 also automatically adjusts gain to the sensor and outputs such gain to output processor 251. The output processor 251 generally cancels out the effects caused by the gain adjustment from the detected signal to produce an output signal which corresponds to the sensed beam intensity. In the illustrated embodiment, the output processor also offsets the output data so that it corresponds to a "calibrated" gain value. These general mechanisms are further described below.

The measurement block 250 includes control-voltage amplifier 64 in a feedback loop with logarithmic amplifier 182 and PMT 10. The photomultiplier tube (PMT) receives a PMT gain from the control-voltage amplifier 64. The PMT 10 converts the light impinging thereon into an electrical signal 68 having a current value that is proportional to the light intensity, which signal 68 is sent to the logarithmic amplifier 182. The logarithmic amplifier 182 produces a signal which is the log of the anode current of PMT 10. Any suitable base value may be utilized by the logarithmic amplifier 182. In one implementation, the logarithmic amplifier 182 is a four-decade log amplifier (such as a model 382 logarithmic amplifier available from Analog Modules, Inc. of Longwood, Fla.). The log amplifier's output is sensed by a PID (proportional, integral, and differential) controller 184 and compared to a reference voltage. When the signal is below Vref, the PID controller 184 increases the input to high-voltage amplifier 64 which in turn increases the PMT gain until the log signal matches Vref or the maximum tube gain is reached. When the output of log amplifier 182 is above Vref, the PMT gain is diminished until the signal again matches Vref or the minimum PMT gain Vmin is reached. The normal operating range of Vctrl is between Vmin and Vmax (typically from about −25 to about −75 volts).

A PID controller generally allows one to create a control voltage which is any linear combination of the proportional, integral, and differential components of the input signal. One implementation of the PID controller 184 employs a commercially-available limiting operational amplifier, such as a Model AD8036 available from Analog Devices of Norwood, Mass., to constrain the output of the PID controller to a predefined range. Its output drives the input of amplifier 64. When such a limiting amplifier is used, the limits VminRef and VmaxRef are set as inputs to the amplifier as shown in FIG. 4 so that the output of amplifier 64 is never driven beyond the voltage range of Vmin and Vmax.

In addition to the usual PID control functions, our PID controller also supports an "open loop" mode, which copies an externally applied signal to the PID controller's output when enabled. This open loop mode allows the gain of the PMT to be externally controlled to facilitate the gain calibrations.

The effect of compensation circuit 186 is to inject into the anode 68 of PMT 10 a current which substantially cancels the current injected from amplifier 64 by the parasitic capacitances within the tube. One embodiment of a compensation circuit is further described below with reference to FIG. 10.

Figure 5:
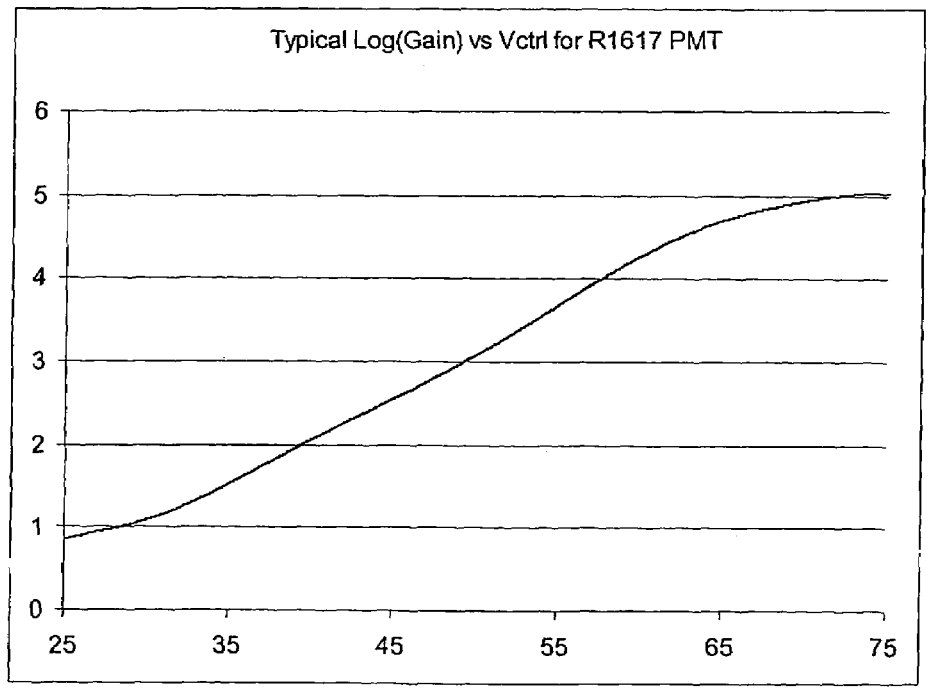
FIG. 5 is a graph illustrating the typical gain response as a function of Vctrl, for a R1617 PMT, biased at 650 Volts.

FIG. 5 is a graph illustrating the typical gain response as a function of Vctrl, for a R1617 PMT, biased at 650 Volts. It may be seen that the response is nearly a straight line in log-linear space, over about 4 orders of magnitude in gain. This degree of gain modulation is accomplished with a control voltage swing of approximately 50 volts. In addition, the control voltage is near ground. No control signals need to be sent across the large bias voltage to the cathode side of the PMT. This combination of relatively low voltage swing and near ground potentials enables the design of a simple and high-speed feedback loop to control the tube gain.

Because the actual gain characteristics of a PMT may differ from the curve in FIG. 5 or because of errors in logarithmic amplifier 182 or because of current dependant errors originating elsewhere, such as in the PMT itself, the outputs of linear amplifier 190 and logarithmic amplifier 182 of FIG. 4 are digitized and transformed into ideal logarithmic representations of the detected signal and gain. In the illustrated embodiment, the outputs of linear amplifier 190 and logarithmic amplifier 182 are separately digitized by ADCs 204 and 202, respectively. Their outputs are used to interrogate programmable look up tables (LUT's) 208 and 206, respectively. As will be appreciated by persons of ordinary skill in the art, lookup tables 208 and 206 are used to implement completely general calibrations which convert the outputs of amplifiers 190 and 182 into ideal logarithmic representations of gain and anode current having a common pre-determined base.

As will be readily appreciated by persons of ordinary skill in the art, the lookup tables 206 and 208 would be experimentally determined for individual particular embodiments of the invention to remove any offsets, gain-errors, or higher order non-linearities in the circuits or the PMT. Depending on the actual gain characteristics of the particular type of PMT being used, a logarithmic amplifier, or an amplifier with some other non-linear transfer function, such as a power law (e.g., square root, cube root, etc.) may be substituted for amplifier 190 without altering the substance of the invention.

The output of lookup tables 208 is digitally subtracted from the output of lookup table 206 in arithmetic logic unit (ALU) 210 to produce a digitized log-light-level output signal of the same predetermined base.

In an optional implementation, the illumination intensity can be independently measured, converted to a logarithm, and then simply subtracted from the log-light-level signal to get the log-scattering-amplitude signal. As shown, the illumination level is input through a linear or non-linear (e.g., log) amplifier 201, ADC 203 and LUT 207. This permits the use of noisy lasers (such as shorter wavelength HeCd lasers) and enables the deflector to be run at maximum efficiency throughout the scan, to minimize the quantum-mechanical uncertainty in the measured data.

The majority of defects may be found by detecting contrast, defined as the ratio of the intensities in the target and reference dies, rather than by threshold, which is defined as the difference between the intensities. However, in conventional inspection systems, determining the ratio of the intensities is computationally expensive. By using a logarithmic representation, the difference of the log intensities may simply be obtained to get the log of the intensity ratio (e.g., via the processor or image processor 500 of FIG. 1). A threshold may then be applied to the log-ratio at a value that is equivalent to the desired threshold on the linear ratio to determine whether there is a defect.

The MMD 200 may also include any suitable mechanisms for further transforming the log light signal output from the ALU, depending on the application. In one implementation, the log light signal from the ALU 210 is input to a look-up table (LUT) 212. In one useful application, LUT 212 is configured to either relinearize the log-light-level output signal when fixed mode is selected and to retain the log light level output when the adaptive mode is selected. That is, the output LUT 212 implements a saturating exponential function, defined by f(x)=min(A+B*exp(C*x), K) for suitable values of the constants A, B, C and K, in the fixed mode and an identity function or noise compensating function in the adaptive mode. Typical values for A, B, C and K may be 3.0, 2.21978E-4, 3.59779E-04 and 4095 respectively. In the fixed mode, the output LUT 212 allows the inspection tool to emulate conventional linear detector hardware. A programmable offset may also be added to the logarithmic data, by adding a fixed value to all the entries in one of the LUTs 206, 207 or 208, to emulate the gain control that was provided by the PMT voltage in previous inspection tools. That is, a user's PMT gain selection is emulated by selecting a corresponding offset value for the data coming out of ALU 210. In the illustrated embodiment, an OFFSET signal is added to the contents of LUT 207. Alternatively, the contents of the output LUT 212 may be shifted to account for a user selected PMT gain.

With these emulation mechanisms, the end user, and even the high level software, cannot distinguish between true linear hardware and the MMD hardware running in emulation mode. Switching between logarithmic and linear modes is extremely fast, since multiple pre-defined look-up tables can be paged in and out of service by changing one address register which is input to LUT 212 as a "Fixed/Adaptive Mode" signal. The ability to perform relinearization is a tremendous benefit because it allows reuse of existing calibration, wafer alignment and registration mechanisms, and recipes from previous generation tools. For example, a user could continue to inspect production wafers in linear mode, while using their existing Statistical Process Control parameters, to keep their line running. By then immediately rescanning the same wafers in adaptive mode, they can establish new SPC parameters for the more sensitive operating mode and unambiguously qualify the new measurement technique on production wafers, prior to actually releasing it to production. Calibration may be performed in any suitable manner. For example, in fixed mode, one may inspect a sample having a known intensity (linear) value under a first set of operating conditions. When the measured linear output is not equal to the expected intensity, the operating conditions are adjusted. The operating conditions continue to be adjusted until the measured linear output equals the expected intensity value. When the measured output matches the expected intensity value, the calibration is complete.

Each LUT (e.g., 206, 207, 208, or 212) may be embodied within any suitable memory. By way of examples, each LUT may be implemented by an SRAM, DRAM, ROM, PROM, EPROM, EEPROM, non-volatile RAM, or flash memory.

Figure 6A:
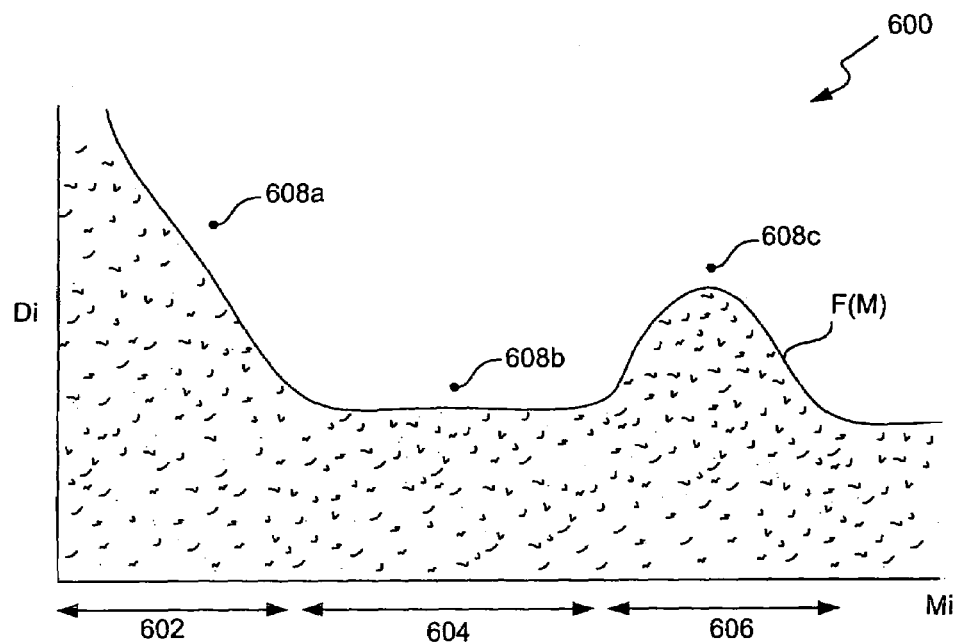
FIGS. 6A through 6D illustrate a noise compensation technique in accordance with one embodiment of the present invention.

The inspection systems of the present invention may also include noise compensation mechanisms. That is, the output data may be transformed on the fly to compensate for noise introduced from a number of sources. The noise may include shot noise, electronic noise, and pattern noise. FIGS. 6A through 6D illustrate a noise compensation technique in accordance with one embodiment of the present invention. Initially, two representative dies (referred to as target and reference dies), which are assumed to be error free, are scanned. These two scans are used to form a scatter plot 600 as shown in FIG. 6A. The scatter plot 600 is a graph of the absolute difference (or square of the difference) between the intensity value for each location i of the two dies ($D_i$) as a function of the average intensity value for the two dies for each location ($M_i$). $D_i$ and $M_i$ are calculated by equations [1] and [2]:

$$Di = |Ti - Ri| \quad [1]$$

$$Mi = \frac{Ti + Ri}{2} \quad [2]$$

where T is the target die's intensity and R is the reference die's intensity. The average intensity value $M_i$ for the two dies at a particular location i is a measure of the true value of how bright that location i is supposed to be. Thus, the scatter plot shows the uncertainty in the measurement as a function of the true intensity. As shown, the scatter plot shows three sources of noise: shot noise 602, electronic noise 604, and pattern noise 606 (e.g., from a grainy metalic line).

The points of scatter plot of FIG. 6A are then used to calculate the envelope function f(m) (as shown in FIG. 6A) from the distribution of data. The envelope generally encompasses the points of the scatter plot without encompassing any stray points, such as points 608a–c, which are located a significant distance from the majority of points. One technique for creating the envelope is to divide the graph into regions (e.g., 50 or 100 vertical slices) and compute the average value for $D_i$ within each slice. One then interpolates between those average values for each slice. After the envelope f(m) is calculated, a normalization function $N(M_i)$ is calculated based on the envelope f(m). The normalization function is calculated by equation [3]

$$N(Mi) = \frac{Fo}{f(Mi)} \quad [3]$$

where $F_o$ is the average value of f(m). The data may then be transformed using the normalization function $N(M_i)$ as shown in FIG. 6B:

$$Ei = Di \times N(M_i) \quad [4]$$

Figure 6B:
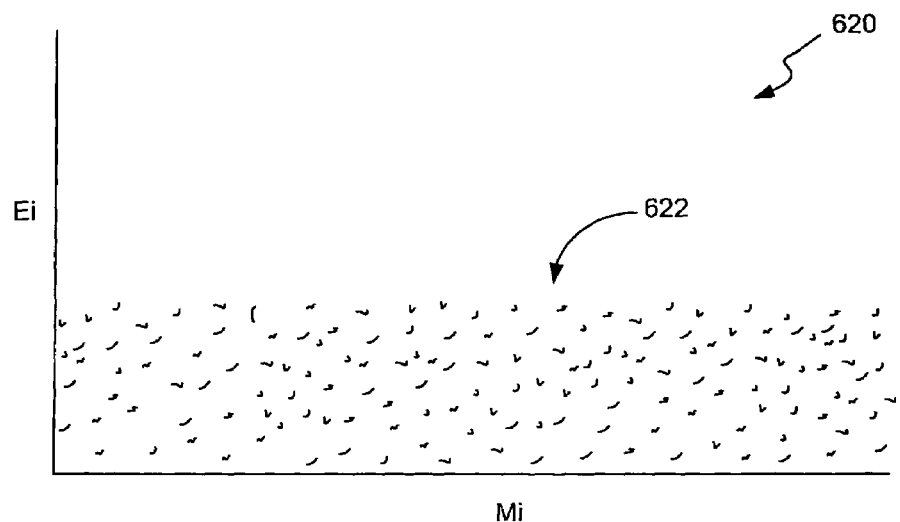

The scatter plot of FIG. 6B presents a uniform noise floor 622. A single threshold that is suitably high above the noise level may be set for data $E_i$, since the noise structures have been normalized to a flat level. Thus, the defects may be efficiently determined as points located significantly higher than the uniform noise floor (above the single threshold value). That is, the interesting defects are above the noise floor. In contrast, the different noise structures of FIG. 6A require three different threshold levels for the three different noise levels or noise areas to detect the three different defects 608a–c. For example, if a single threshold is set high enough to catch the defect 608a above the shot noise, the defect 608b above the electronic noise floor and the defect 608c above the pattern noise are missed.

Figure 6C:
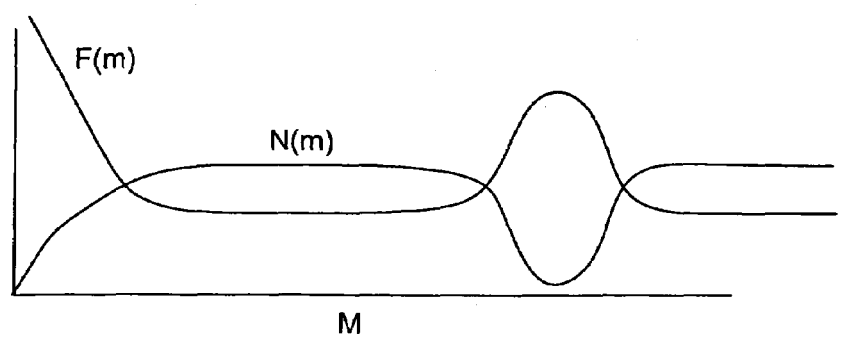
Figure 6D:
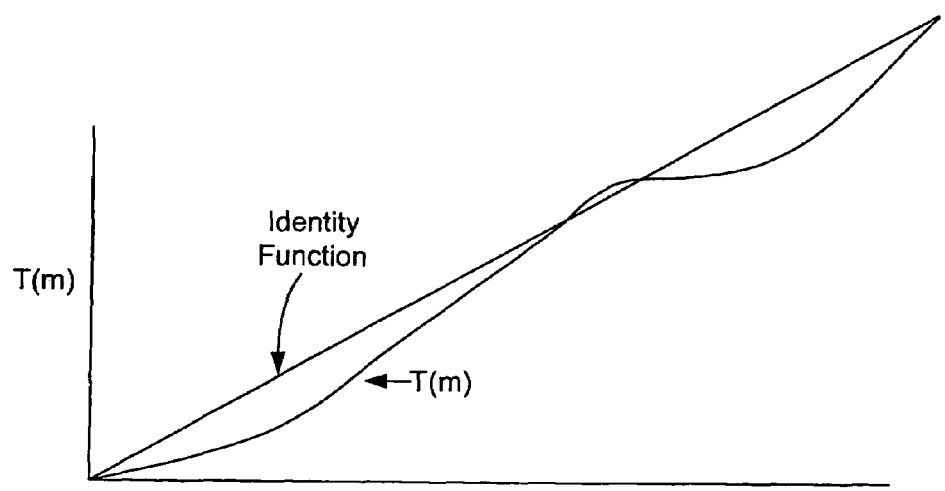

The normalization of the data may be implemented by configuring the output LUT (e.g., LUT 212 of FIG. 4) so that the derivative of the output from the output LUT is equal to the normalization function N(Mi). Thus, the transformation function T(x) of the output LUT (i.e., the contents of the output LUT) may be calculated by equation [5]:

$$T(x) = k + \int N(x) dx \quad [5]$$

Where the value k is chosen to center the values of T(x) within the allowed numerical range of the output LUT. FIG. 6C is a graph of both the envelope function $f(M_i)$ and the corresponding normalization function $N(M_i)$ of FIG. 6A as a function of $M_i$. FIG. 6D is a graph of an example transformation function $T(M_i)$ as a function of $M_i$, plotted along side an identity transformation function. As shown, the transformation function $T(M_i)$ has different slopes which correspond to intensity values having different associated noise levels. Said in another way, the local slope of the output LUT acts as a gain value that is to be applied to different output data values. Accordingly, the different noise levels are made uniform by the transformation function $T(M_i)$. Note that in the special case where the noise structures were already uniform prior to the data transformation, the normalization function N(x) would equal 1 and result in $T(M_i)$ equaling the identity function.

The data generated by conventional inspection systems was conventionally divided into different ROI's according to their respective threshold values. In contrast, when noise is accounted for in the output LUT, there is no need for "regions of interest" (ROI) to be defined in order to analyze the detected data. Accordingly, the compensation techniques presented herein greatly simplify the data analysis since only a single threshold may be used to analyze the output data.

The inspection system embodiments of the present invention allow for significant increases in dynamic range. An inspection system utilizing the MDD of FIG. 4 results in 6 orders of magnitude. An increased dynamic range for the defect data, in effect, allows additional information to be tracked about each defect, as compared with conventional inspection systems with a lower dynamic range. Thus, the ability of an ADC (automatic defect classification) system to identify defects is significantly increased. Techniques for implementing ADC are described further in U.S. Pat. Nos. 6,104,835 and 5,991,699 and International Application WO0140145, which patents and applications are incorporated herein in their entirety. Also, the process insight given by an SPC (statistical process control) summary is enhanced. Improvements in the inspection hardware and software have made the following additional information available for use by the ADC and SPC systems:

1. Absolute scattering fraction of the defect.
2. Absolute scattering fraction of the reference die.
3. Statistical significance of the defect.
4. Region of Interest in which the defect occurs.

Binning the defects separately for each ROI and/or using some linear, non-linear or logical combination of the other variables to classify the defects will increase the value of information that is ultimately presented to the customer.

The enhanced dynamic range of the MDD of the present invention allows the elimination of apriori gain settings for the inspection tool. Determining the optimal trade-off between saturation and lack of gain on previous instruments has historically been a very time consuming and subjective task. Eliminating this step greatly simplifies the task of setting up a wafer inspection recipe.

Figure 7:
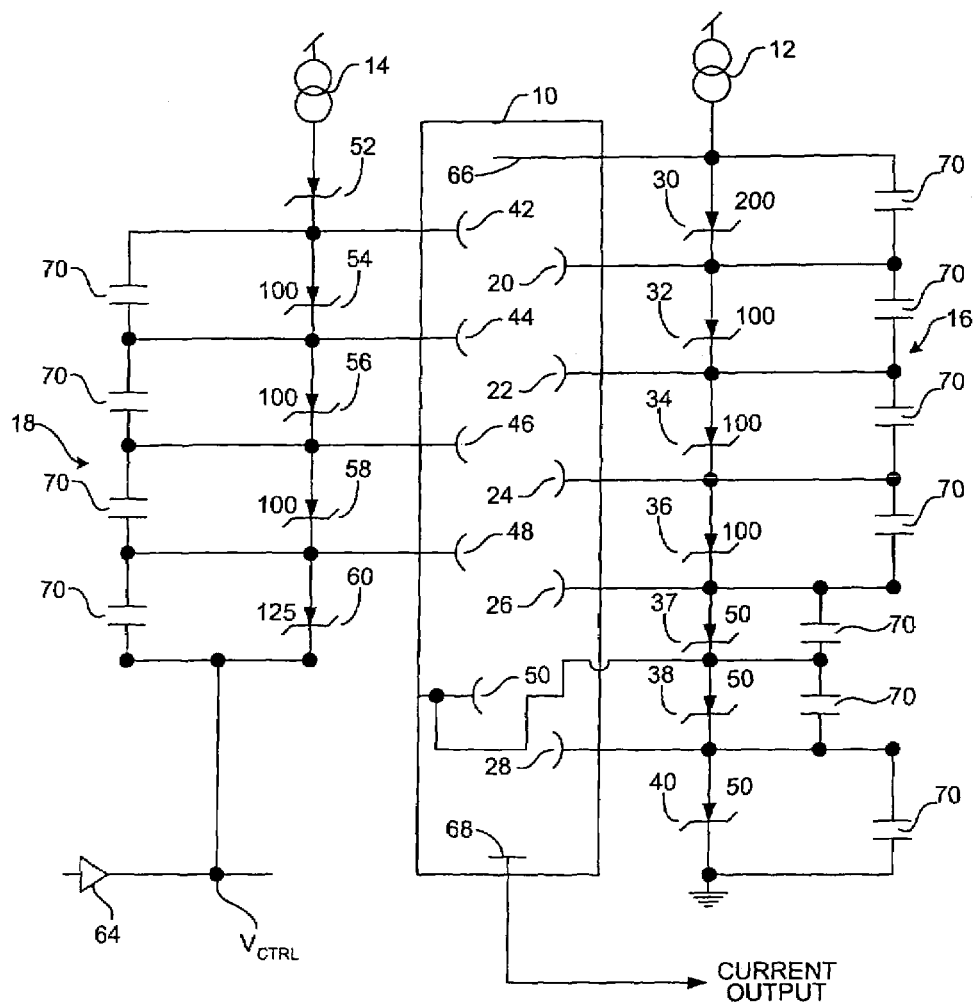
FIG. 7 is a schematic diagram illustrating the biasing circuit for a photomultiplier tube (PMT) according to a specific embodiment of the present invention.

Detail example implementations of the MDD of FIG. 4 will now be described. Any suitable mechanism to bias the PMT 10 may be used. Several embodiments of a biasing mechanism are described in U.S. Pat. No. 6,002,122, which patent is incorporated herein by reference in its entirety. Referring now to FIG. 7, a schematic diagram illustrates biasing of a PMT according to a specific embodiment of the present invention. As shown, a PMT 10, such as the Hamamatsu R1617, furnished with ten dynodes, is depicted, although persons of ordinary skill in the art will appreciate that the invention could easily be adapted to PMT's from different manufacturers or having different numbers of dynodes.

The PMT 10 is biased by two matched constant current sources 12 and 14 which drive two separate bias strings 16 and 18, one for the modulated and one for the fixed dynodes. The bias zener diode string 16 for dynodes 20, 22, 24, 26, 50, and 28 includes series-connected zener diodes 30, 32, 34, 36, 37, 38, and 40 driven by constant current source 12, and is referenced to ground. These zener diodes preferably have voltage ratings of 200V, 100V, 100V, 100V, 50V, 50V and 50V respectively.

The other bias zener diode string 18 for dynodes 42, 44, 46 and 48, includes series connected zener diodes 52, 54, 56, 58 and 60, driven by constant current source 14. Bias zener diode string 18 is referenced to a fast variable voltage source, Vctrl at the output of amplifier 64. These zener diodes preferably have voltage ratings of 150V, 100V, 100V, 100V and 125V respectively. Even though Vctrl may vary rapidly, the constant current sources driving the bias strings require only fixed DC voltages to operate.

As will be appreciated by persons of ordinary skill in the art, the values of the zener diodes 30, 40, 52, and 60 are chosen to offset the voltages at adjacent dynodes such that the voltage between adjacent dynodes decreases from the voltage at the cathode 66. Furthermore, when Vctrl is equal to 1.5 times the voltage on dynode 28, this voltage is called Vmax, the maximum gain control voltage.

Since the inter-dynode voltage within each of the two bias zener diode strings is constant, capacitors 70 may be placed in parallel with all the bias zener diodes, except zener diode 52, to lower the dynamic impedance of the bias strings. These capacitors can be made arbitrarily large, (i.e., 0.1 .mu.F) without affecting the speed of the gain control circuit disclosed herein.

When Vctrl is equal to Vmax, the PMT 10 operates at its maximum gain. As Vctrl is made less negative, the inter-dynode voltages become alternately larger and smaller than their conventional values of a conventional biasing circuit. For example, as Vctrl is made less negative, the potential between dynodes 48 and 26 decreases while the potential between dynodes 48 and 24 increases. Therefore the gain at each dynode alternately increases or decreases. However, the gain decreases faster on the even dynodes than it increases on the odd dynodes. As a result, the overall PMT gain decreases.

As Vctrl approaches 0.5 times the voltage on dynode 28, the pairs of odd and even dynodes approach the same voltage and the overall tube gain is minimized. This voltage is called Vmin. As Vctrl approaches Vmin, the system becomes less accurate, due to component mismatches in the two bias strings. However, the circuit will still continue to attenuate the signal. This enables built in overload protection, with a fast recovery when the overload ends.

Figure 8:
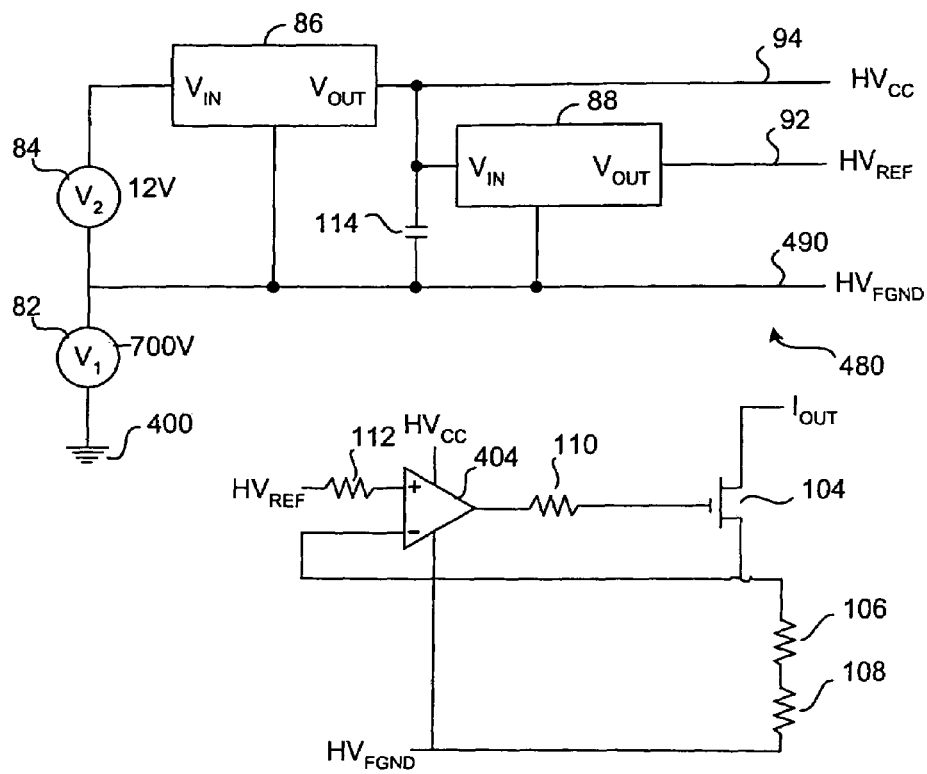
FIG. 8 is a schematic diagram illustrating the accurate matched current sources of FIG. 7 in accordance with one embodiment of the present invention.

The accurate matched current sources 12 and 14 of FIG. 7 needed to drive the two bias strings can each be implemented in any suitable manner, e.g., as shown in circuit 480 of FIG. 8 using only two fixed voltage supplies, high voltage supply 82 and low-voltage supply 84, connected as shown. Unlike the supplies used with conventionally biased PMTs, the HV supply need not be particularly stable, because the current source acts as series regulator. High-voltage supply 82 may be a commercially-available high-voltage supply, such as a Model E06 available from EMCO High Voltage of Sutter Creek Calif., and low-voltage supply 84 may be a commercially-available 12V DC-DC converter with a high isolation voltage, such as a Model UWR-12/250-D12 available from DATEL of Mansfield Mass. Voltage regulator 86 is a standard 3-terminal linear voltage regulator supplying a regulated voltage of 9 volts. Voltage regulator 88 is a precision 3 terminal voltage reference providing a voltage reference of 4.096 volts. Lines 490, 92, and 94 are used to power the remainder of the circuit elements of FIG. 8. High-voltage power supply 82 forms a high voltage "floating" ground, HVFGND at line 490, for the current sources. Low-voltage power supply 84 and voltage regulators 86 and 88 are referenced to this floating ground to generate the 4.096V reference voltage at line 92 and the 9 volt supply at line 94 used by the current source.

Amplifier 404 is a moderate-speed, low offset, operational amplifier and MOS transistor 104 is a high-voltage low capacitance N-channel MOSFET. These devices are well known commodities to any person of ordinary skill in the art, and suitable alternatives are available from numerous manufacturers, including Linear Technology, Analog Devices, BurrBrown, Supertex, Zetex, Motorola and National Semiconductor.

Resistor 106 is a precision 3,000 ohm, 0.1% resistor (Panasonic) which is added to Resistor 108, an ordinary 1% 150 ohm resistor. Amplifier 404 adjusts the voltage at the gate of MOS transistor 104 to maintain a constant 4.096 volts across the 3,150 ohm combination of resistors 106 and 108 to HVFGND. This results in a precise 1.300 mA current flowing through MOS transistor 104. Since the gate of MOS transistor 104 is isolated, all the current must come from the load, at the drain of MOS transistor 104.

Resistors 110 and 112, and capacitor 114 are used, according to standard design practices, to correct for non-ideal behavior in the components. Resistor 110, which may have a value of about 50 ohms in the embodiment shown, isolates amplifier 102 from the gate capacitance of MOS transistor 92. Resistor 112, which may have a value of about 3,160 ohms in the embodiment shown, compensates for the input bias current of amplifier 90. Capacitor 114, which may have a value of about 1 $\mu$F in the embodiment shown, is a decoupling capacitor.

Figure 9:
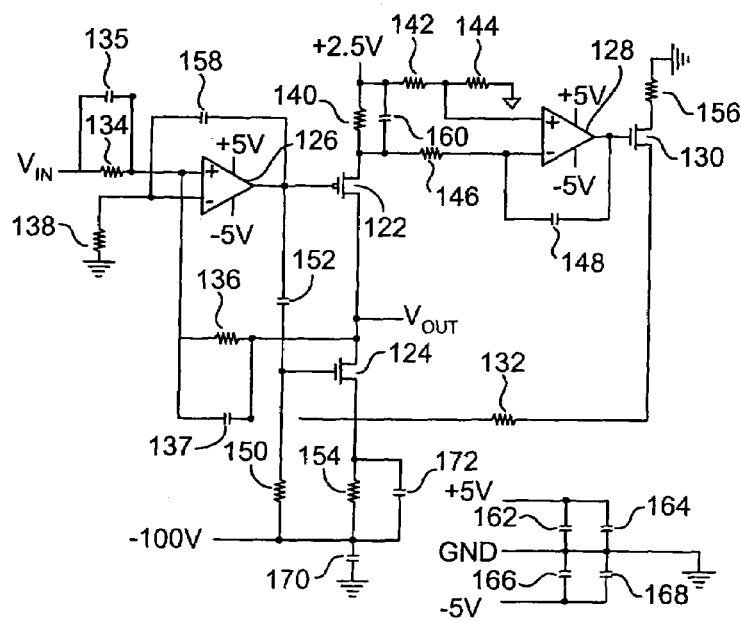
FIG. 9 is a schematic diagram showing one implementation of the amplifier circuit 64 of FIGS. 4 and 7.

In the illustrated embodiment, the high voltage amplifier 64 of FIG. 7 is a high-speed linear amplifier with a gain of about 35. FIG. 9 is a schematic diagram showing one implementation of the amplifier circuit 64 of FIGS. 4 and 7. Amplifier circuit 64 of FIG. 9 uses three power supplies and one voltage reference (not shown), having nominal output voltages of +5V, +2.50V, −5V and −100Vrespectively. The output is driven by high voltage MOS transistors 122 and 124 which are wired in a high-gain, common-source configuration. To minimize drain capacitance, the normal operating range of the output is restricted to −25V to −75V. Amplifier 126 controls MOS transistor 122 directly, but only controls the high-frequency part of MOS transistor 124. The DC component of MOS transistor 124 is controlled by amplifier 128, through transistor 130 and resistor 132. Amplifier 128 actively adjusts the bias of MOS transistor 124 to maintain a constant source current on MOS transistor 122. By configuring the circuit so that the constant source current on transistor 122 is slightly larger than the largest possible current supplied to the load, it is ensured that transistor 124 is always slightly forward biased.

Restricting the operating range of the circuit of FIG. 9 and using active biasing ensures that neither MOS transistor 122 nor MOS transistor 124 is ever driven into saturation, or allowed to completely shut off. This enables a very fast amplifier to be built.

Using an active biasing circuit minimizes power consumption by carefully tracking changes in the power supply voltages and automatically compensating for changes in the threshold voltages of any of the MOS transistors. If conventional biasing schemes were used, the system would have to be designed for the worst case combination of component values and supply voltages. This means that under normal operation the power consumption would be significantly higher.

Resistors 134 and 136 set the DC gain of the amplifier, while capacitors 135 and 137 are selected to reduce the impedance of the feedback network while maintaining the same gain value at high frequencies. Resistor 138 compensates for input bias current in amplifier 126. Resistor 140 senses the DC bias current of MOS transistor 122. Resistors 142 and 144 set the reference voltage used to set the bias current of transistor 122. Resistor 146, together with capacitor 148, limits the bandwidth of the bias amplifier 128. Resistor 132 isolates the gate of MOS transistor 124 from the output capacitance of MOS transistor 130. Resistor 150 is a pull-up resistor to keep capacitor 152 charged. Resistors 154 and 156 limit the loop gain of bias amplifier 128 to prevent oscillations.

Capacitors 148 and 158, having values of 0.1 .mu.F and 30 pF, respectively in the illustrated embodiment, are bandwidth limiting feedback capacitors, needed for stability. Capacitor 152, having a nominal value of 0.1 .mu.F in the embodiment illustrated, is a DC blocking capacitor needed to allow amplifier 126 to control MOS transistor 124 even though it is outside the +/−5V operating range of amplifier 126. Capacitors 160, 162, 164, 166, 168, 170 and 172 are all bypass capacitors, and have nominal values of 0.1 .mu.F in the embodiment illustrated.

Figure 10:
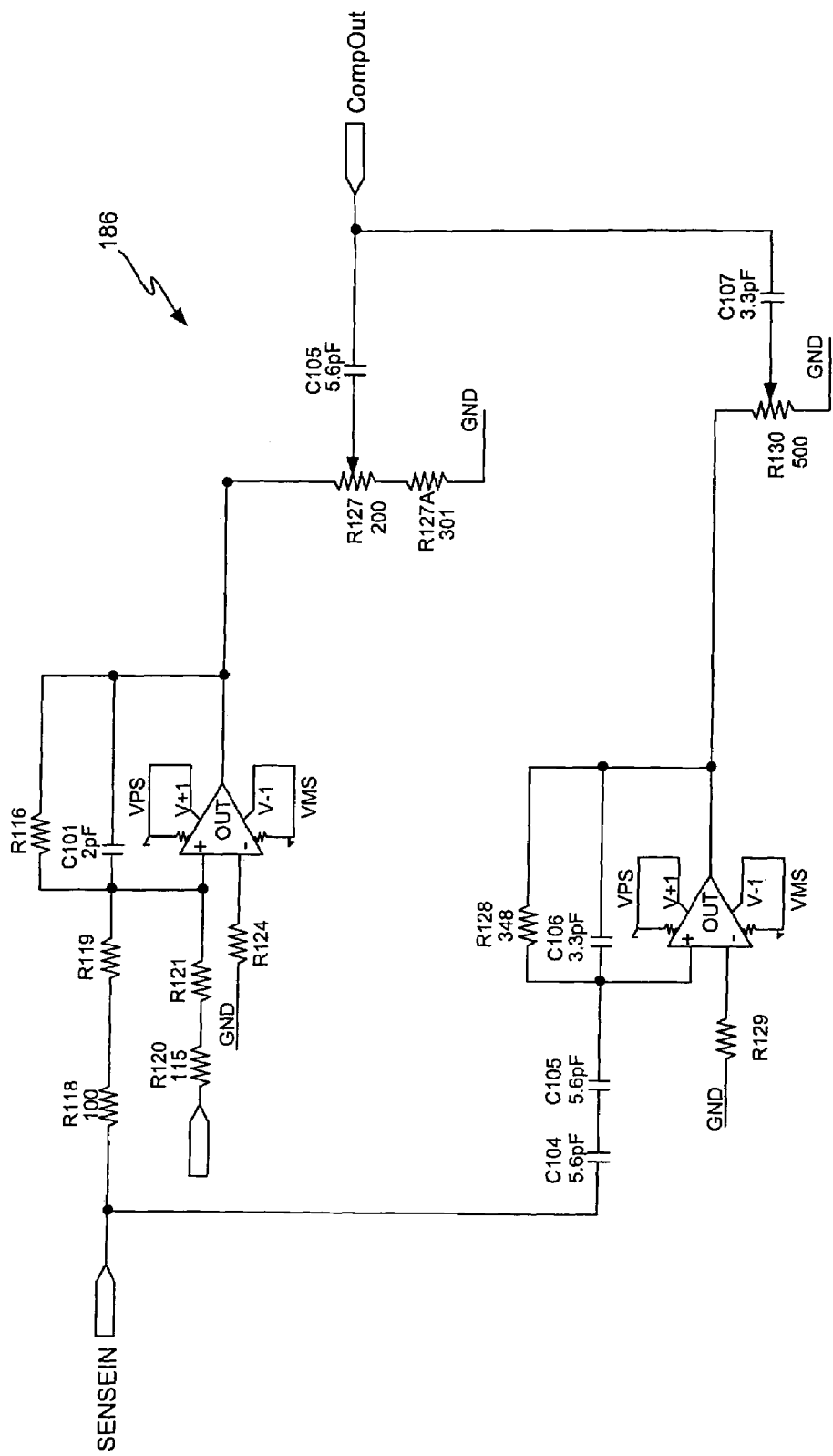
FIG. 10 is a schematic diagram illustrating the compensation circuit of FIG. 4 as being implemented with two derivative compensation circuits in accordance with one example implementation of the present invention.

The compensation circuit 186 of FIG. 4 may be implemented in any suitable manner. In one implementation, first and second derivative compensation circuits are utilized. (Of course, any number of derivative compensation circuits may be utilized). FIG. 10 is a schematic diagram illustrating the compensation circuit 186 with first and second derivative compensation circuits in accordance with one example implementation of the present invention. The input SENSEIN, which originates from the output of amplifier 64 of FIG. 4, is received into a linear amplifier U20. Variable resistor R127 forms a voltage divider, which presents a selectable fraction of the output of U20 to C103. This fraction typically is in the range of 60% to 100%. C103 then generates a current into the node CompOut which is proportional to the first derivative of the input voltage SENSEIN. The proportionality constant is the gain of amplifier U20 times the value of C103 times the fractional setting of R127. In this way, amplifier U20, potentiometer R127, and their associated resisitors and capacitors form a first derivative compensation circuit. Preferably, the compensation circuit 186 includes a second derivative compensation circuit in the form of U22, R130, and their associated resistors and capacitors. Like the first derivative compensation circuit, the second derivative circuit also capacitively couples into the output CompOut through potentiometer R130 and capacitor C107. However, the input stage of the second derivative circuit differs from the input stage of the first derivative compensation circuit. The input stage of the second derivative circuit includes capacitors C104 and C105 in place of resistors R118 and R119 in the input stage of the first derivative circuit. These capacitors serve to take another derivative of the input signal SENSEIN, resulting in an output current that is proportional to the second derivative of the input voltage.

An alignment procedure may be performed to adjust the compensation circuit to optimum values. Under zero light conditions, a control voltage (e.g., a sine wave of suitable frequency and amplitude) may be injected into the control amplifier 64 while a suitable DC bias current is injected into logarithmic amplifier 182 of FIG. 4. The two potentiometers R127 and 130 are then adjusted to minimize the RMS value of the AC component of the current measured by logarithmic amplifier 182. When the AC component of the logarithmic amplifier's current is minimized, the compensation circuit 186 is optimized.

A fine mesh dynode photomultiplier tube, such as the fifteen-dynode Hamamatsu R3432-01, may be used in the present invention in place of the conventional photomultiplier tube. These photomultiplier tubes have shorter transit times, higher pulse linearity, and better immunity to magnetic fields than conventional photomultiplier tubes. It is likely that such tubes are not currently in common usage because, with their small surface area, the mesh dynodes are particularly susceptible to damage from sustained overload signals. The present invention is able to make good use of their strong points, and also protect them from overload damage.

Alternatively, a PMT may be customized to meet particular specifications limits that are suitable for the requirements of the application. In a darkfield application, the specifications may include limiting the manufacturing variation in the PMT gain at a fixed voltage, limiting the parasitic capacitance between one or more dynodes and the anode, and limiting the cathode resistivity. In one implementation, PMT gain range is limited to a 2:1 variation. Resistivity limits may be selected based on the trade off between quantum efficiency and nominal resistivity values. Coupling capacitance limits may be selected as an acceptable trade off between manufacturability of the PMT and the confidence level in a compensation circuit used with the PMT to accurately correct for error currents introduced by the coupling. Customization of the PMT may also include inserting wires in the PMT cathode and/or evaporating a pattern of metal lines on to the glass under the cathode to reduce the effects of sheet resistance and inserting shielding structures, shortening or re-routing wires, or making other changes to the dynodes and interconnect geometry to minimize the parasitic capacitance between one or more of the dynodes and one or more of the other dynodes or the anode.

Other types of sensor technologies may be used in place of the PMT. For example, any one of a number of other sensor technologies that provide intrinsic and variable gain may be used in place of the Photo Multiplier Tube. Such technologies include: Electron Multiplier Tubes, microchannel plate PMTs, Avalanche Photodiodes, Metal Channel Dynode PMTs, Wire Mesh Dynode PMTs, PMTs with explicit gate or grid electrodes and imaging arrays with programmable integration times.

Figure 11A:
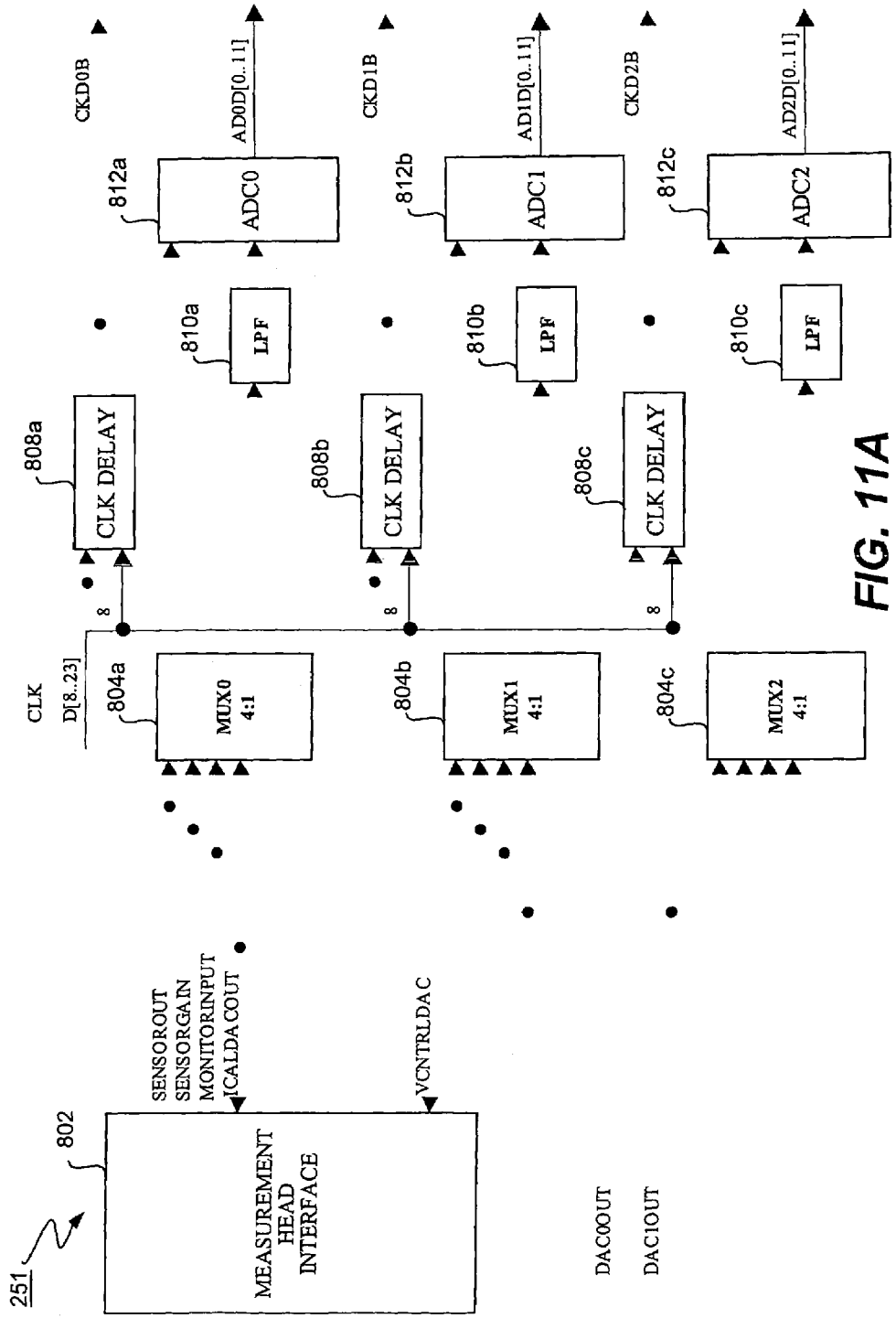
FIGS. 11A through 11C show a more detailed schematic diagram of the output processor of the mixed mode detector (MDD) of FIG. 4 in accordance with one embodiment of the present invention
Figure 11B:
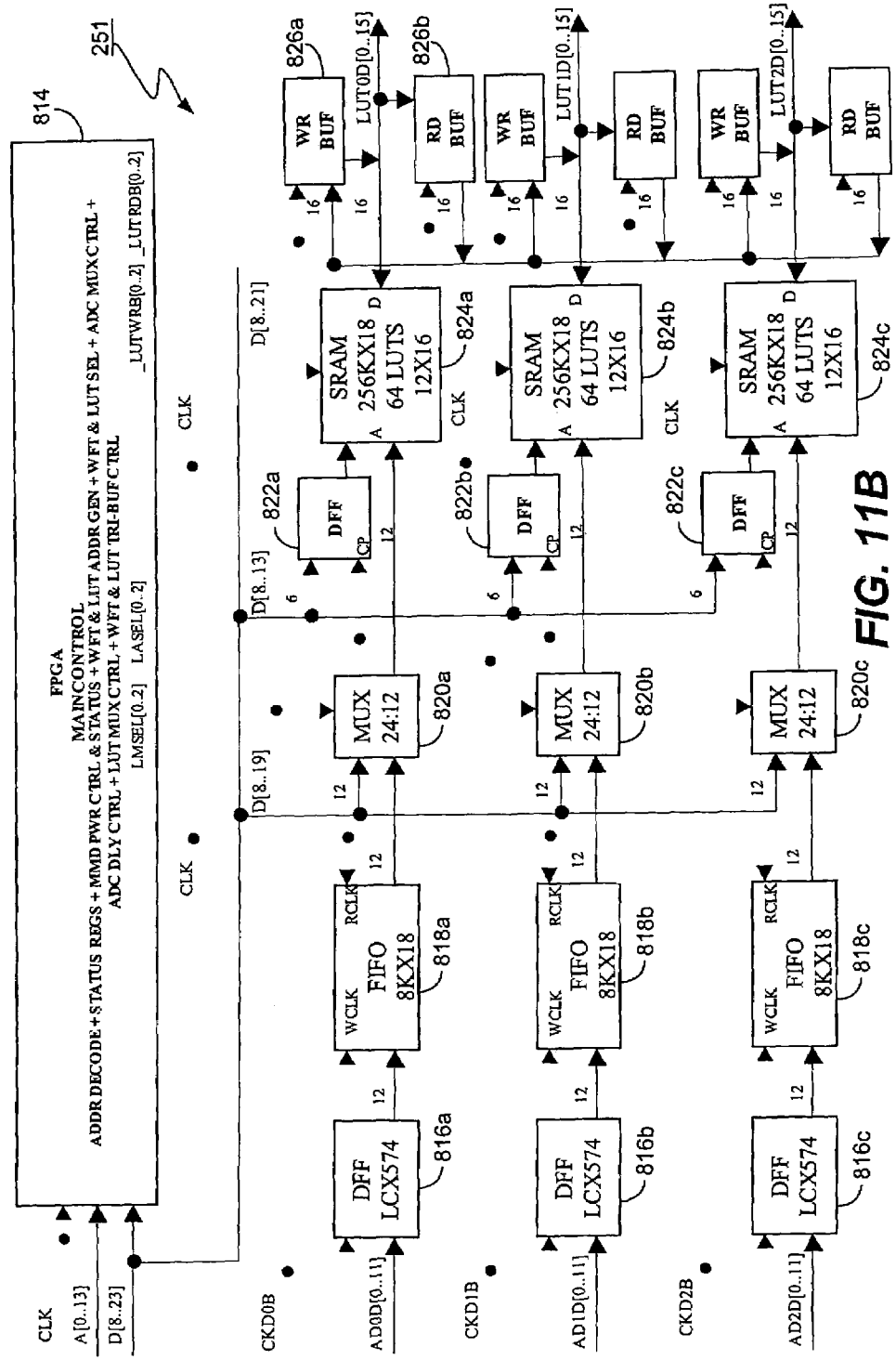
Figure 11C:
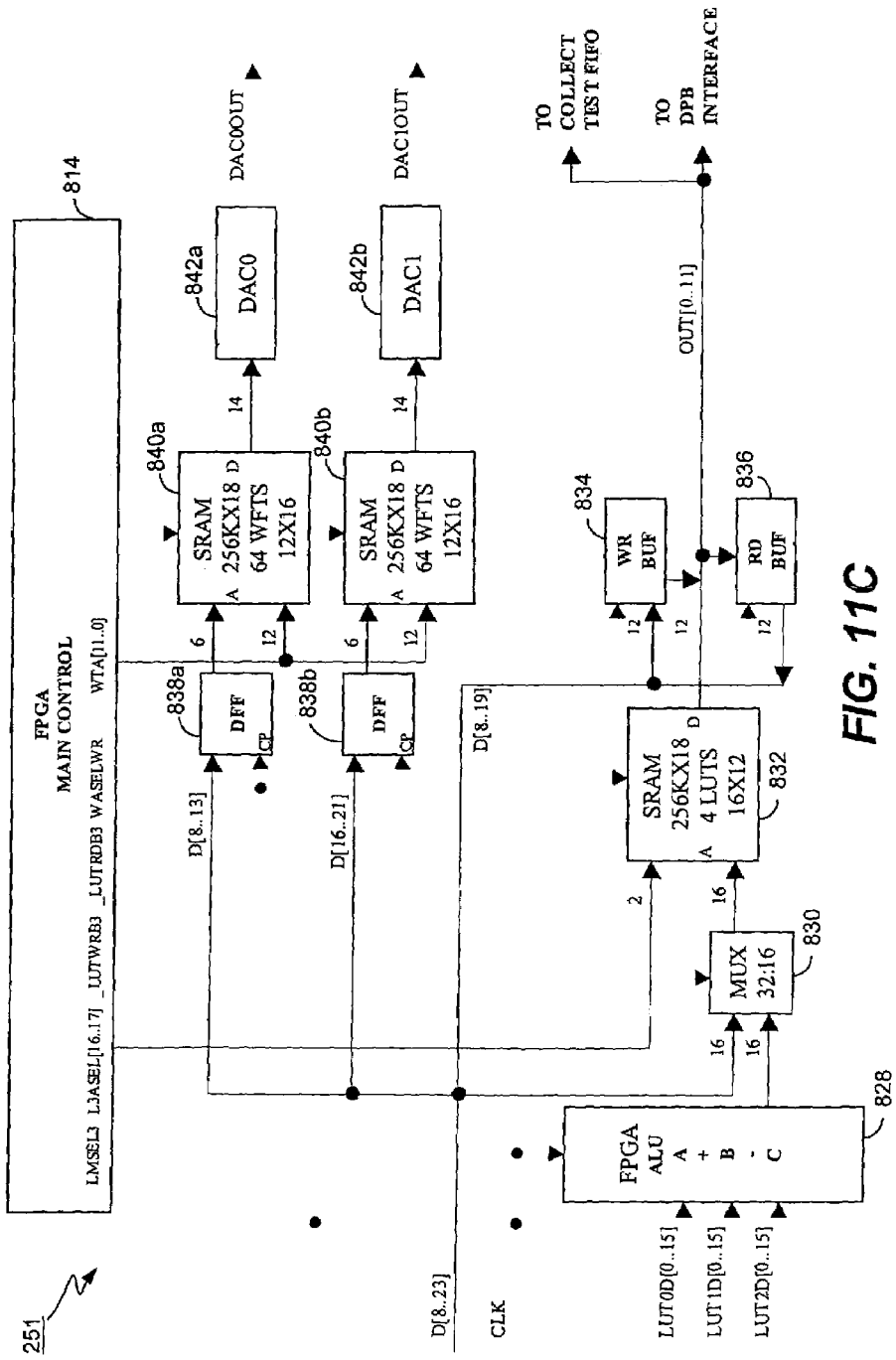

FIGS. 11A through 11C show a more detailed schematic diagram of the output processor 251 of the mixed mode detector (MDD) of FIG. 4 in accordance with one embodiment of the present invention. As shown, the output processor 251 includes a measurement head interface 802 for interfacing with the measurement block 250 of FIG. 4. In FIG. 11A, the measurement head interface outputs SENSOROUT, SENSORGAIN, and MONITORINPUT to three multiplexers (MUX) 804*a–c*. The SENSOROUT signal corresponds to the logarithmically amplified output from the sensor; the SENSORGAIN corresponds to the amplified sensor gain; and MONITORINPUT corresponds to the log of an illumination level (e.g., as described above with respect to FIG. 4). Referring to FIG. 4, SENSORGAIN is the output of linear amplifier 190, and SENSOROUT is the output of logarithmic amplifier 182. The MONITORINPUT line may alternatively be used to input other relevant signals. For example, as described below with respect to FIGS. 13A and B, the MONITORINPUT signal is the output of the beam monitor circuit 860.

Returning to FIG. 11A, MUX 804*a* outputs the SENSOROUT signal to low pass filter (LPF) 810*a*. Similarly, MUX 804*b* outputs the SENSORGAIN signal to LPF 810*b*. MUX 804*c* outputs the MONITORINPUT signal to LPF 810*c*. The LPF's 810 limits the bandwidth of their respective signals to thereby at least meet the bandwidth requirements of their respective ADC's. Each data signal (e.g., SENSOROUT, SENSORGAIN, and MONITORINPUT) is converted from an analog to a digital signal by its corresponding ADC 812. Thus, the output of ADC 812*a* is a digital SENSOROUT signal; the output of ADC 812*b* is a digital SENSORGAIN signal; and the output of ADC 812*c* is a digital MONITORINPUT signal.

Clock delays 808*abc* and FIFO buffers 818*abc* serve to effectively provide a delay for the analog signals received into each LPF without having to endure the signal distortions which are inherent in programmable analog delay lines. The clock components 808*abc* may be programmable clock delay lines, similar to model 3D7408 from Data Delay Devices of Clifton N.J. The clock delays 808*abc* delay the propagation of a logic clock signal over a 64 nS range with 0.25 resolution. By delaying the time when the analog signal is digitized and clocked into the FIFO buffer, the amount of time the data "waits" in the FIFO before being clocked out and used by the ALU is reduced. By implementing independent programmable delays for each signal, the relative phase of the SENSOROUT and SENSORGAIN signals can be adjusted. For some embodiments of the MMD, careful tuning of the relative signal phase may be used to properly recombine the two signals into an artifact free representation of the optical signal. By way of example, when the gain input to the PMT, from amplifier 64 of FIG. 4, changes there is an inherent delay between the time when the gain change is applied to the PMT and the time when the effect of this gain change is observed at the PMT output. Additionally, the propagation delay of the LPFs 810*abc* may vary from instance to instance of the MMD, due to production tolerances in the components used. Calibrating the programmable delay values for each instance of the MMD corrects for these production variations.

The delay for each signal through its corresponding LPF and ADC pair may be calibrated in any suitable manner. In one embodiment, a sample having a known intensity pattern is utilized to determine such delay. A pattern having a stark contrast, such as a street (i.e., the dark area between the dies) in a bright region works well. In this example, the incident beam (e.g., laser) is scanned across the street, causing the PID controller to rapidly vary the sensor (e.g., PMT) gain. Since the intensity of the detected signal is expected to form a square wave, it is a straightforward calibration exercise to try a number of different delay values within a reasonable range of expected values and choose the delay value which minimizes the observable artifacts in the output of the MMD. This chosen delay value may then be stored in software and programmed into the clock components 808 as the calibrated delay value.

Referring to FIG. 11B, each data output from FIG. 11A is propagated through a series of standard components: a D flip-flop 816, a FIFO 818, and a MUX 820. Each MUX may funnel the data output from the ADC's of FIG. 11A into a corresponding SRAM 824. Alternatively, Main Control Block 814 may be configured to work with each MUX 820 and WR_BUF (e.g., 826*a*) to facilitate writing into its associated. SRAM 824. For instance, an OFFSET value (e.g., which corresponds to a PMT gain value which was set by a user for calibration purposes) may be input to and passed through SRAM 824*c* in place of the MONITORIN-PUT. Main Control Block 814 is also configured to work with each MUX 820 and RD_BUF (e.g., 826*b*) pair to read from its corresponding SRAM 824.

ADC's 812*a–c* correspond to ADC's 204, 202 and 203 of FIG. 4. SRAM 824*a*, 824*b*, and 824*c* are example implementations of LUT 208, LUT 206, and 207, respectively, of FIG. 4. Each SRAM or LUT 824 receives specific data as an address which corresponds to specific look-up data. Each SRAM or LUT 824 then outputs the corresponding look-up data for each specific input data. The SRAM's provide an extremely efficient mechanism for transforming the output data of the inspection system for various purposes, such as simplifying data processing or facilitating various calibrations or noise compensation techniques, etc. In this specific embodiment, each LUT effectively converts 12 bit input data to 16 bit input data which allows one to eliminate rounding error that may result from a particular transformation as well as increasing the data's resolution.

Referring to FIG. 11C, the SRAM or LUT signal are then input to ALU 828, passed through MUX 830, into SRAM 832 which corresponds to an implementation example of the output LUT of FIG. 4. In the illustrated embodiment of FIG. 11C, the output SRAM 832 transforms 16 bit data into 12 bit data using any suitable transformation function. This downgrading of the number of bits may be necessary in some inspection systems due to legacy software and/or hardware which is configured to use a particular data word size, e.g., 12 bit. The Main Control Block 814 works with MUX 830 and WR_BUF 834 and RD_BUF 836 facilitate reading and writing from and to output SRAM 832.

D flip flops 838, SRAMs 840, and DAC's 842 provide a mechanisms for determining values for the sensor gain calibration LUT and the sensor output calibration LUT Each SRAM 840*a* and 840*b* includes data which may be selectively output and input to a corresponding DAC 842 which converts the data into a corresponding analog signal. As shown, DAC 842*a* outputs DAC0OUT signal which optionally controls a variable current source built into amplifier 182, when one or more special calibration modes are enabled. DAC 842*b* outputs DAC1OUT signal which controls the output of the PID 184, when one or more special calibration modes are enabled. These signals may be varied by outputting different SRAM data from different addresses. The sensor output calibration LUT may be determined by disabling any light sources striking the sensor and then measuring the output due to a series of known currents injected into amplifier 182 by its internal calibration current source. Once the sensor output LUT has been determined, the sensor gain calibration LUT may be determined by injecting a series of known optical stimuli into the sensor from the instrument and varying the gain of the detector using DAC 842*b* and the "open Loop" calibration mode of the PID 184. Measuring the change in the sensor output as the gain is varied will determine the contents of the sensor gain calibration LUT.

Referring back to FIG. 1, each of the collector channel 510*ab*, 511*ab* and 521 may include other components for performing additional optical operations on the scattered light, which components are not illustrated so as to not obscure the invention. For example, each collector channel 510*a–b* and 511*a–b* may include a lens system that collects and directs the scattered light. For instance, a series of mirrors may be used to reflect the light so that it is imaged onto PMT 10. Positioned at the Fourier transform plane is a programmable spatial filter and a variable aperture stop. The programmable spatial filter allows the system to take advantage of spatial filtering when periodic features on the surface 12 are scanned. Also located proximate to the Fourier transform plane is a variable polarization filter. It should be noted, that it is also possible to place a PMT directly at the Fourier transform plane.

In an alternative embodiment, an MDD may be implemented with non-linear electronics, such as a logarithmic amplifier, placed between the PMT and ADC. Benefits may be obtained even without an automatic gain adjustment circuit. Non-linear amplification mechanisms positioned between the PMT and ADC tend to compress the dynamic range of the signal output from the PMT to make it more closely matched to the dynamic range of the ADC, which is usually much lower than the dynamic range of the PMT. If the non-linearity is monotonic and calibrated, the non-linearity may then be inverted digitally and as a result significantly extend the effective measurement range. Suitable compressive non-linearities include logarithms, power laws of the form $y=x^a$ where a is in the range of 0 to 1. (The special cases where $a=\frac{1}{2}$ and $a=\frac{1}{3}$ are readily recognized as the square-root and cube-root functions respectively). Noise compensation techniques may also be efficiently implemented on a non-linear output as described above.

Figure 12:
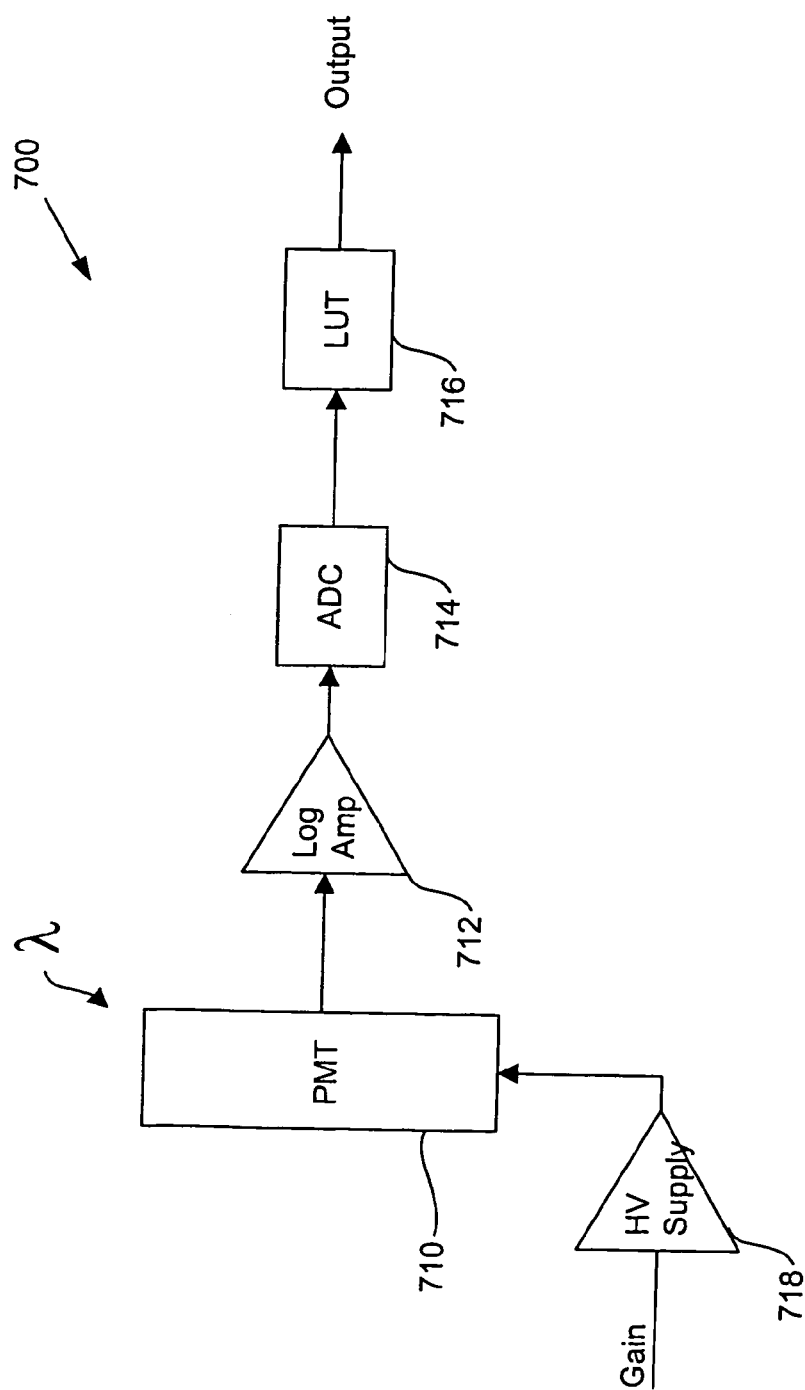
FIG. 12 is a schematic diagram of an alternative MDD implementation having non-linear electronics placed between the PMT and ADC in accordance with one embodiment of the present invention.

FIG. 12 is a schematic diagram of an alternative MDD implementation having non-linear electronics placed between the PMT and ADC in accordance with one embodiment of the present invention. As shown, the gain to PMT 710 is determined by high voltage power supply and conventional bias network 718. The output from PMT is received by logarithmic amplifier 712. The output of logarithmic amplifier is then input to ADC 714, which may then output digital data to LUT 716 or else send it directly to the data processor 500 of FIG. 1.

It has been discovered that a conventional logarithmic amplifier circuit design will work unusually well in this application. Classic transistor-in-the-feedback-loop based log-amp designs are not commonly used in practice, because of their problems with amplitude dependant bandwidths, reverse biased inputs, and temperature dependant offset voltages at the input. However, when a PMT is used as the signal source all these limitations are either overcome or exploited to our benefit. First, the ideal-current source behavior of the PMT negates the effects of input offset voltages. In addition, the inherent unipolar nature of the PMT (it can be thought of as a kind of vacuum tube diode) eliminates reverse bias problems, as long as an FET input op-amp is used. Finally, the amplitude dependent bandwidth can be used to implement a sophisticated noise compensation technique. By choosing a suitable gain level for the PMT, we can arrange for the bandwidth of the log-amp to begin dropping at precisely the signal amplitude where the photon shot noise is starting to rise above acceptable levels. By lowering the bandwidth, we raise the integration time of the amplifier. This higher integration time serves to average out the shot noise to get a more accurate measurement of the background intensity. Implementing this type of adaptive image processing in digital hardware is computationally expensive. Because of this, having such an adaptive bandwidth characteristic intrinsic to the analog electronics is a significant benefit.

Since the detected signal is represented logarithmically (as is the gain in the gain adjustment embodiment of FIG. 4), one may also easily extend the dynamic range of the inspection system by modulating the illumination or incident beam intensity based on the sensor gain adjustment. That is, the sensor or PMT gain adjustments may be utilized to adjust the illumination power. For example, this may be accomplished by directly modulating the intensity of the scanning beam either in response to the measured light level or adjusted gain level or based on prior knowledge of the die's optical scattering characteristics. By way of examples, the laser intensity may be modulated directly, the efficiency of the AOD may be modulated, or an explicit variable attenuator placed in the illumination or collection path may be modulated. Any suitable combination of hardware and/or software may be utilized to implement techniques for adjusting the illumination level.

Figure 13A:
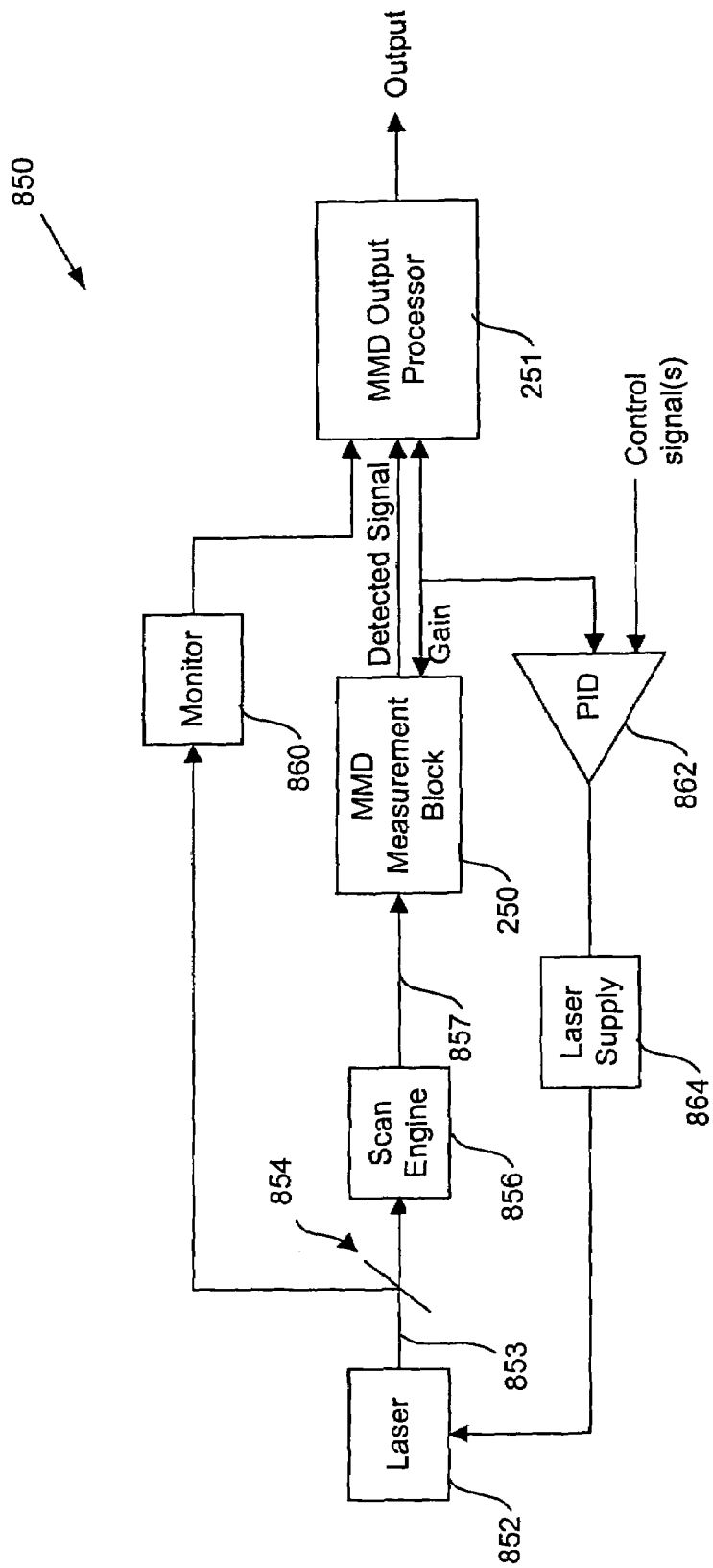
FIG. 13A is a diagrammatic representation of an inspection system having a mixed mode detector that also automatically adjusts illumination power in accordance with one embodiment of the present invention.

FIG. 13A is a diagrammatic representation of an inspection system 850 having a mixed mode detector (e.g., blocks 250 and 251) that is utilized to automatically adjust illumination power in accordance with one embodiment of the present invention. As shown, the system 850 includes a laser 852 for generating a beam 853. Beam splitter 854 directs a first beam portion of the beam to monitor 860 and a second beam portion to scan engine 856. Scan engine operates to scan the beam across a sample. Suitable laser generator and scan engines are described above with respect to FIG. 1.

The monitor 860 may generate a illumination level signal (e.g., with a PMT and amplifier) based on the input laser beam and output the illumination level signal to MDD output processor 251. Likewise, a beam 857 emitted from the sample is input to MMD measurement block 250. The emitted beam may be in the form of scattered light, for example. As described above, the MDD measurement block 250 generates an amplified detected signal from the emitted beam based on an adjusted gain signal. The MDD measurement block 250 also includes mechanisms for automatically adjusting the gain for the sensor (e.g., PMT) and amplifying the adjusted gain signal before it is output to the MDD processor 251.

The amplified gain signal is input to a PID 862 which is configured with one or more control signal(s) to provide an adjusted laser power signal to laser supply 864. The laser supply 864 inputs a laser supply to laser 852 to adjust the power level of the laser beam. Accordingly, the laser's power may be continually adjusted based on a continually adjusted PMT gain. For example, when the gain increases, the laser power is raised to increase the optical signal entering the MMD, which in turn will result in a stabilizing (negative feedback) reduction in the gain of the MMD.

Adjustments to the laser power will, of course, cause fluctuations in the detected light intensity. One may factor out these fluctuations by dividing out the laser power adjustments from the final output signal. Towards this end, the laser level is provided by monitor 860 to MDD output processor 251. The MDD output processor 251 then transforms the laser level to a logarithmic value and subtracts this log laser level from the detected signal. Thus, the laser level changes are effectively divided out of the final output signal of the MDD processor 251. This mechanism may be implemented in any suitable manner. In the embodiment of FIGS. 11A through 11C, the laser power signal may provide the MONITORINPUT signal to the MDD processor 251.

Figure 13B:
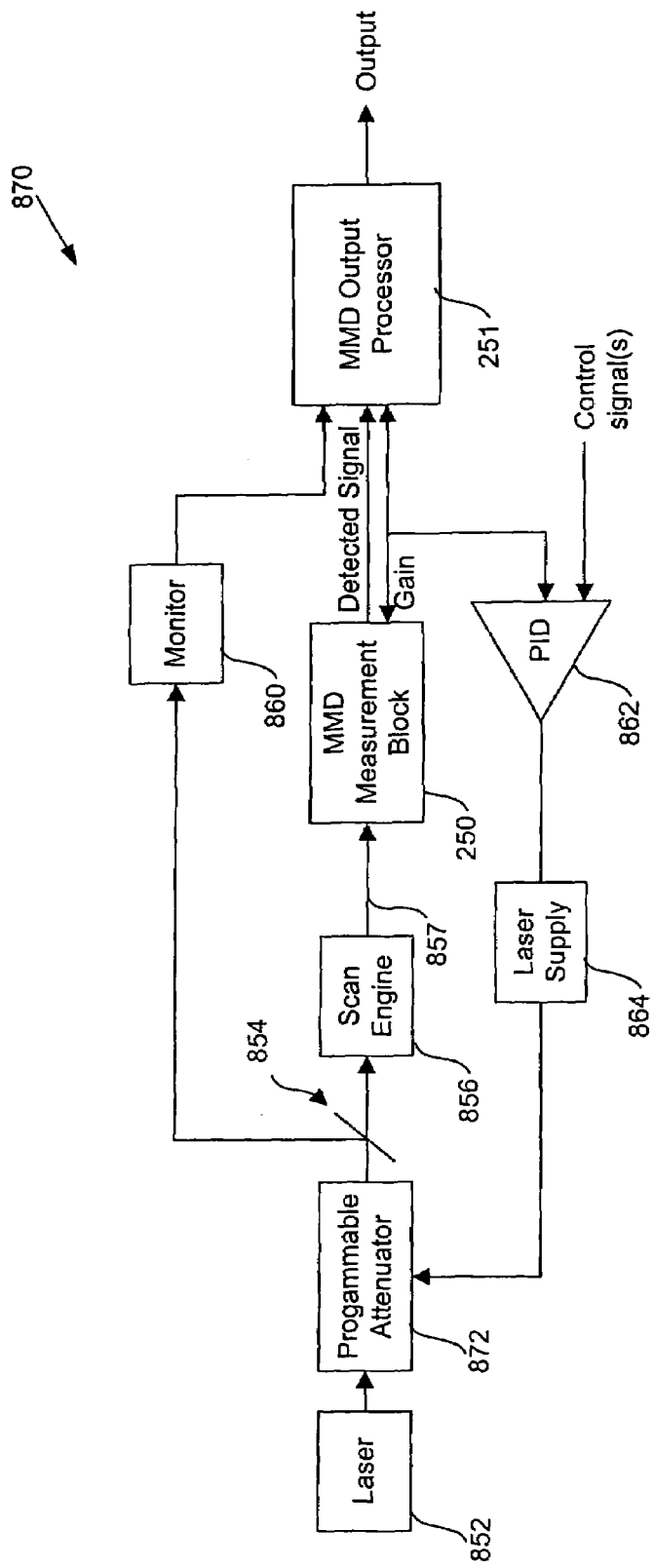
FIG. 13B illustrates an alternative embodiment of an inspection system having a mixed mode detector that automatically adjusts illumination power.

FIG. 13B illustrates an alternative embodiment of an inspection system 870 having a mixed mode detector (e.g., blocks 250 and 251) that is utilized to automatically adjust illumination power. Instead of adjusting the laser supply that is applied to the laser generator 852, a programmable attenuator 872 is placed within the optical illumination path to thereby adjust the illumination beam's power after it is output from the laser generator 852. One may wish to modulate an attenuator because such modulation typically has a higher range and/or a faster adjustment rate than directly modulating the laser supply.

Figure 14:
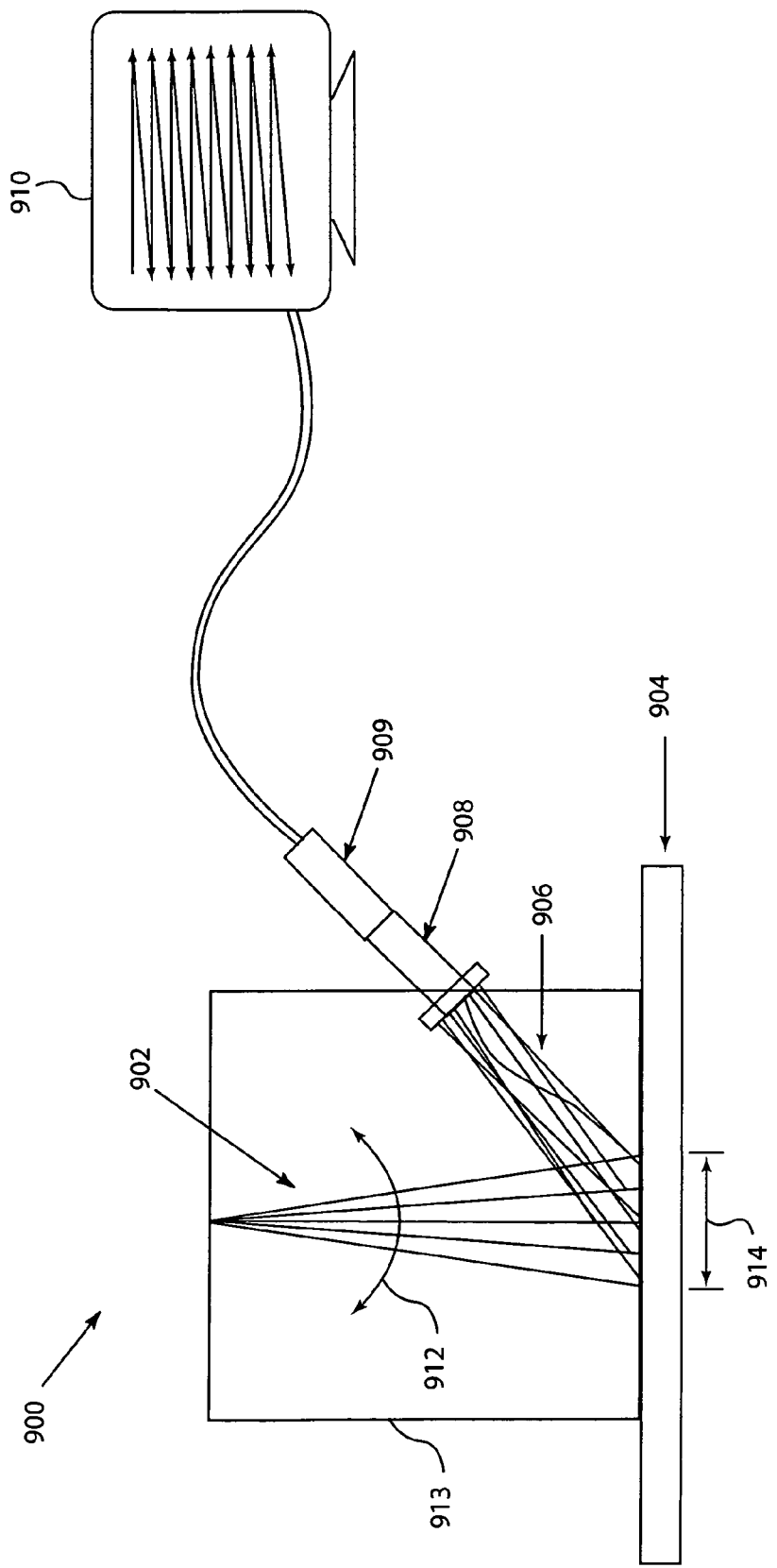
FIG. 14 is a diagrammatic representation of a scanning electron microscope (SEM) having a mixed mode detector (MDD) in accordance with one embodiment of the present invention.

FIG. 14 is a diagrammatic representation of a scanning electron microscopy (SEM) configuration 900 in accordance with one embodiment of the present invention. As shown, column 913 generates and directs a beam of electrons 902 to be scanned over a specimen 904 (e.g., a semiconductor wafer). Multiple raster scans 912 are typically performed over a small area 914 of the specimen 904. The beam of electrons 902 either interacts with the specimen and causes an emission of secondary electrons 906 or bounces off the specimen as backscattered electrons 906. The secondary electrons and/or backscattered electrons 906 are then detected by a scintillator 908 which converts the detected electrons into photons. The scintillator output is fed to mixed mode detector (MDD) 909 which is coupled with a computer system 910. The MDD 909 may take the form of any of the MDD embodiments described herein. The computer system 910 generates an image that is stored and/or displayed on the computer system 910. The column 913 may take any suitable form for generating and directing a beam across specimen 904. Additionally, the scintillator 908 and MDD 909 may be incorporated within any suitable type of SEM system. Several embodiments of a suitable SEM system are described in U.S. Pat. No. 6,066,849, which patent is incorporated by reference herein in its entirety.

Figure 15:
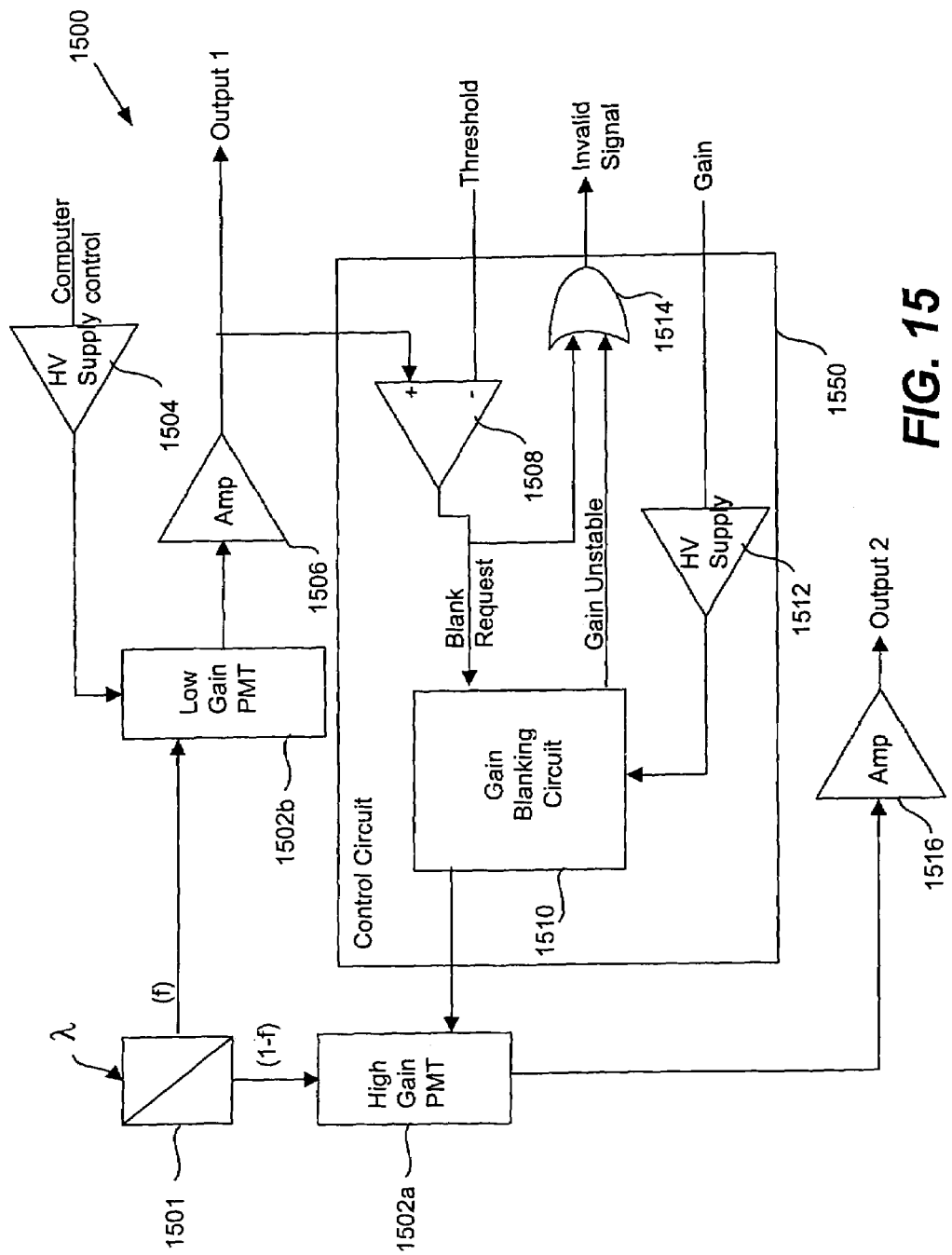
FIG. 15 is a diagrammatic representation of a dual sensor high-dynamic range Photo-Detector in accordance with an alternative embodiment of the present invention.

FIG. 15 is a diagrammatic representation of a dual sensor high-dynamic range Photo-Detector 1500 in accordance with an alternative embodiment of the present invention. In general terms, this detector 1500 includes a lower gain PMT 1502*b*, as well as a high gain PMT 1502*a*. As shown, a beam splitter 1501 sends a small fraction (F) of the optical signal to the low gain PMT 1502*b*. Typical values of F are between about 5 and about 10 percent of the optical signal although other values may be used. The two PMT's 1502 are then digitized separately, with the low gain PMT 1502*b* being used to sense defects in bright regions of the wafer. The low gain PMT 1502*b* is also used to switch off the high gain PMT 1502*a* to thereby protect it from overload signals until the lower gain "sentinel" PMT 1502*b* (and low gain channel circuitry) indicates that it is safe to switch the high gain PMT 1502*a* back on.

Any suitable high speed switching circuit, with rise and fall times in the range of about 10 to about 100 nanoseconds, may be utilized within the control circuit 1550 to indicate when the high gain PMT 1502*a* should switch off (or directly turn the PMT 1502*a* off). As shown, the output of each PMT 1502 may feed into a conventional linear transimpedance amplifier, e.g., as described above. The output of the low gain PMT 1502*b* feeds into amplifier 1506, and the output of the high gain PMT 1502*a* feeds into amplifier 1516. A direct analog circuit feeds back from the amplifier of the sentinel PMT (e.g., 1502*b*) amplifier to a control circuit 1550 which controls the high gain PMT (1502*a*).

The control circuit 1550 may include any suitable components for regulating the gain to the high gain PMT 1502*a*, switching off the high gain PMT 1502*a* when the PMT output gets too high, and outputting an Invalid Signal to indicate the state of the high gain PMT 1502*a*. As shown, the control circuit 1550 includes a comparator 1508 which receives the amplified output from the low gain PMT 1502*b* and a threshold value. The comparator 1508 outputs a "Blank Request" Signal. The Blank Request signal is "0" when Output 1 is lower than the threshold value, and "1" when Output 1 is equal to or higher than the threshold.

A Gain Blanking Circuit (or high speed switching circuit) 1510 receives the Blank Request Signal and output from a high voltage (HV) power supply 1512. The Gain Blanking Circuit provides the output from the HV power supply 1512 to the high gain PMT 1502a when the Blank Request Signal is low. When the Blank Request Signal is high, the Gain Blanking Circuit 1510 rapidly switches off the high gain PMT 1502a by reverse biasing a grid electrode or one or more dynodes within the PMT. The Gain Blanking Circuit 1510 may also output a "Gain Unstable" Signal when the gain for the high gain PMT is switched off, is in the process of switching on or off, or is suffering from signal artifacts generated by a recent gain transition. The Blank Request Signal and Gain Unstable Signal may be fed into an "OR" circuit 1514 which outputs the Invalid Signal. Alternatively, the Blank Request Signal may only be output as the Invalid Signal. Any suitable fast binary gain switching circuit may be used for the Gain Blanking Circuit 1510. Several embodiments are described in U.S. Pat. No. 4,820,914, issued 11 Apr. 1989 and U.S. Pat. No. 5,076,692 issued Dec. 31, 1991, which patents are incorporated herein by reference in their entirety.

The "Invalid Signal" flag generally indicates whether data from the high gain PMT is reliable. In general, the signal from the higher gain PMT is preferred for image processing, when it is reliable. When the optical input becomes so bright that data from the high gain PMT is not reliable, data from the lower gain PMT may still be used to perform defect detection in the bright regions.

The amplified signals from each PMT may be digitized separately by an ADC (not lo shown) to N-bit resolution. Any suitable value may be used for N, such as 8, 12, or 16. The ADC outputs and the Invalid Signal may then be analyzed by any suitable technique to detect defects. In one embodiment, the output signals for the low and high gain PMT's 1502 are analyzed separately. However, defects found from the high gain PMT output are only reported for regions where the Invalid Signal flag is low in both the target and reference image. In regions where data from either the target or reference die is invalid for the high gain PMT, defect detection can still be done using the data from the lower gain PMT.

In an alternative embodiment, the digital data from both ADC's are recombined into a single extended dynamic range data word prior to image processing. This technique minimizes the computational burden by avoiding parallel processing of the two output signals independently. In this embodiment, operating voltages for the two PMTs are selected so that the ratio of the effective gains, taking the PMT gain and beam splitter efficiency into account, is precisely the Mth power of two. Typical operating values of M are 3–7. Note: The exact operating voltages for the PMTs would be determined by a prior in-system calibration procedure.

During operation, in regions where the Invalid Signal flag is low, the output data word is taken as the ADC value from the high gain PMT, padded with M zeros on the MSB (Most Significant Bit) side. In other regions, where the Invalid Signal flag is high, the output word is taken as the ADC value from the sentinel PMT, shifted toward the MSB by M bits, and padded with zeros on the LSB (Least Significant Bit) side.

Once the output data word has been selected, the Signal Invalid flag can be ignored by the image processing system. Slight variations in the location of the switching point should not, by themselves, cause false counts. Note that for higher values of M the dynamic range of the output data words is extended further, but at the cost of increased granularity in the output data words just above the switching point. The following table indicates the total dynamic range and data granularity for several example values of M and N.

| N  | M  | Dynamic Range (orders of Mag) | Granularity (%) |
|----|----|-------------------------------|-----------------|
| 8  | 3  | 3.31                          | 3.13            |
| 8  | 4  | 3.61                          | 6.25            |
| 8  | 5  | 3.91                          | 12.50           |
| 12 | 4  | 4.82                          | 0.39            |
| 12 | 5  | 5.12                          | 0.78            |
| 12 | 6  | 5.42                          | 1.56            |
| 14 | 6  | 6.02                          | 0.39            |
| 14 | 7  | 6.32                          | 0.78            |
| 14 | 8  | 6.62                          | 1.56            |
| 16 | 8  | 7.22                          | 0.39            |
| 16 | 9  | 7.53                          | 0.78            |
| 16 | 10 | 7.83                          | 1.56            |

While embodiments and applications of this invention have been shown and described, it would be apparent to those skilled in the art that many more modifications than mentioned above are possible without departing from the inventive concepts herein. Routine engineering tradeoffs between speed, power-consumption, noise, sensitivity, and dynamic range will motivate numerous minor design changes as the preferred embodiment disclosed herein is tailored to any given application. The invention, therefore, is not to be restricted except in the spirit of the appended claims.

What is claimed is:

1. An inspection system for detecting defects on a sample, the system comprising:
 a beam generator for directing an incident beam towards a sample surface;
 a detector positioned to detect a detected beam originating from the sample surface in response to the incident beam, wherein the detector comprises:
  a sensor for detecting the detected beam and generating a detected signal based on the detected beam;
  a non-linear component coupled to the sensor, the non-linear component being arranged to generate a non-linear detected signal based on the detected signal; and
  a first analog-to-digital converter (ADC) coupled to the non-linear component, the first ADC being arranged to digitize the non-linear detected signal into a first digitized detected signal,
 wherein the detector further comprises a first feed back circuit for automatically adjusting an illumination intensity of the incident beam based on the non-linear detected signal or the detected signal; and
 a data processor for determining whether there is a defect present on the sample surface based on the first digitized detected signal.

2. An inspection system as recited in claim 1, wherein the sensor is a photomultiplier tube (PMT).

3. An inspection system as recited in claim 1, wherein the sensor is selected from a group consisting of an electron multiplier tube, a micro-channel plate PMT, an avalanche photodiode, a metal channel dynode PMT, a wire mesh dynode PMT, and a PMT with explicit gate or grid electrodes and imaging arrays with programmable integration times.

4. An inspection system as recited in claim 1, wherein the non-linear component is a logarithmic amplifier.

5. An inspection system as recited in claim 4, wherein the detector further comprises a second feed back circuit for automatically adjusting a sensor gain of the sensor based on the non-linear detected signal or the detected signal.

6. An inspection system as recited in claim 5, wherein the second feed back circuit comprises:
  a variable voltage supply component coupled to the non-linear component and arranged to adjust a voltage level of the sensor gain based on non-linear detected signal or the detected signal, a voltage reference signal, and one or more control signal(s); and
  an amplifier coupled to the variable voltage supply and arranged to amplify the sensor gain signal prior to it being input to the sensor.

7. An inspection system as recited in claim 6, wherein the first feedback circuit is arranged to automatically adjust the illumination intensity based indirectly on the first detected signal and based directly on the sensor gain.

8. An inspection system as recited in claim 5, further comprising:
  a second ADC for receiving the sensor gain, digitizing the sensor gain and outputting it as a digitized sensor gain signal;
  a first transformation mechanism for calibrating the first digitized detected signal into a calibrated detected signal;
  a second transformation mechanisms for calibrating the digitized sensor gain signal into a calibrated gain signal; and
  an arithmetic logic unit (ALU) arranged to subtract the calibrated gain signal from the calibrated detected signal to form a first detected output signal,
  wherein the data processor is further arranged to receive the first detected output signal and the step of determining whether there is a defect is based indirectly on the first digitized detected signal by being based directly on the first detected output signal.

9. An inspection system as recited in claim 8, wherein the first and second transformation mechanisms take the form of a look-up table embodied within a memory device.

10. An inspection system as recited in claim 8, further comprising:
  a third transformation mechanism for transforming the first detected output signal into a second detected output signal, the second detected output signal being a relinearized first detected output signal when a mode signal input to the third transformation mechanism indicates a first mode and the second detected output signal equaling the first detected output signal when the mode signal indicates a second mode, and
  wherein the data processor is further arranged to receive the second detected output signal and the step of determining whether there is a defect is based indirectly on the first digitized detected signal by being based directly on the second detected output signal.

11. An inspection system as recited in claim 10, wherein the second detected output signal equals a noise compensating transformation of the first detected output signal when the mode signal indicates a third mode.

12. An inspection system as recited in claim 11, wherein the transformation mechanism operates to cause a derivative of the second digitized detected signal to be equal to a normalization function which is an estimate of the inverse of the noise level or uncertainty in the measurement, and wherein the normalization function is computed by dividing an average of an envelope function by the envelope function itself, and the envelope function is calculated based on an observed repeatability of measurements of the first detected output signal.

13. An inspection system as recited in claim 8, wherein the first and second transformation mechanisms and the ALU have a higher resolution than the first and second ADCs, in order to avoid rounding errors in the transformations.

14. An inspection system as recited in claim 1, the first feedback circuit comprising:
  a power supply for supplying a power level to the beam generator for the incident beam; and
  a variable voltage supply component for receiving the sensor gain, the non-linear detected signal or the detected signal and one or more control signal(s), the variable voltage supply component being arranged to adjust the power level supplied by the power supply so as to adjust the illumination intensity of the incident beam.

15. An inspection system as recited in claim 14, wherein the variable voltage supply component is a proportional integral differential (PID) controller.

16. An inspection system as recited in claim 1, wherein the beam generator comprises a deflector for scanning the incident beam across the sample, and wherein the first feedback circuit adjusts the illumination intensity by adjusting an efficiency of the deflector.

17. An inspection system as recited in claim 1, wherein the beam generator comprises a variable attenuator within a path of the incident beam, and wherein the first feedback circuit adjusts the illumination intensity by modulating the variable attenuator.

18. A method for detecting defects on a sample, the method comprising:
  directing an incident beam towards a first sample surface;
  detecting a first detected beam and generating a first detected signal based on the first detected beam, wherein the first detected beam originates from the first sample surface in response to the incident beam;
  generating a first non-linear detected signal based on the first detected signal;
  digitizing the first non-linear detected signal into a first digitized detected signal;
  analyzing the first digitized detected signal to determine whether it corresponds to a defect on the first sample surface; and
  automatically adjusting an illumination intensity of the incident beam based on the first non-linear detected signal or the first detected signal.

19. A method as recited in claim 18, wherein the illumination intensity is automatically adjusted intensity based indirectly on the first detected signal and based directly on the sensor gain.

* * * * *

UNITED STATES PATENT AND TRADEMARK OFFICE
CERTIFICATE OF CORRECTION

| | | |
|---|---|---|
| PATENT NO. | : 7,012,683 B2 | Page 1 of 1 |
| APPLICATION NO. | : 10/993473 | |
| DATED | : March 14, 2006 | |
| INVENTOR(S) | : Wolf et al. | |

It is certified that error appears in the above-identified patent and that said Letters Patent is hereby corrected as shown below:

On the Title Page: Item (56)

On page 2 of the Title Page, under "Foreign Patent Documents" change "WO01/140145" to --WO01/40145--.

Column 2, line 41, change "farther arranged" to --further arranged--.

Signed and Sealed this

Twenty-eighth Day of November, 2006

JON W. DUDAS
*Director of the United States Patent and Trademark Office*